(12) United States Patent
Fancelli et al.

(10) Patent No.: US 7,803,829 B2
(45) Date of Patent: Sep. 28, 2010

(54) USE OF A KINASE INHIBITOR FOR THE TREATMENT OF PARTICULAR RESISTANT TUMORS

(75) Inventors: Daniele Fancelli, Milan (IT); Antonella Isacchi, Milan (IT); Michele Modugno, Cernusco sul Naviglio (IT); Jurgen Moll, Appiano Gentile (IT); Luisa Rusconi, Milan (IT); Chiara Soncini, Piacenza (IT); Rosita Lupi, Legnano (IT)

(73) Assignee: Nerviano Medical Sciences S.r.l., Nerviano (IT)

( * ) Notice: Subject to any disclaimer, the term of this patent is extended or adjusted under 35 U.S.C. 154(b) by 0 days.

(21) Appl. No.: 12/295,447

(22) PCT Filed: Mar. 29, 2007

(86) PCT No.: PCT/EP2007/053013

§ 371 (c)(1),
(2), (4) Date: Oct. 23, 2008

(87) PCT Pub. No.: WO2007/113198

PCT Pub. Date: Oct. 11, 2007

(65) Prior Publication Data

US 2010/0022532 A1   Jan. 28, 2010

(30) Foreign Application Priority Data

Mar. 30, 2006  (EP) ................................. 06112026

(51) Int. Cl.
*A61K 31/415* (2006.01)
(52) U.S. Cl. .................................................. 514/403
(58) Field of Classification Search .................. 514/403
See application file for complete search history.

(56) References Cited

U.S. PATENT DOCUMENTS

2003/0125359 A1  7/2003  Lyons et al.

FOREIGN PATENT DOCUMENTS

| WO | WO 2004/007504 A1 | 1/2004 |
|----|-------------------|--------|
| WO | WO 2005/074922 A1 | 8/2005 |

OTHER PUBLICATIONS

Shah, Neil P. et al., "Mechanisms of resistance to STI571 in Philadelphia chromosome-associated leukemias", *Oncogene*, Oct. 20, 2003, pp. 7389-7395, vol. 22, No. 47, Nature Publishing Group.
Shah, Neil P. et al., "Overriding Imatinib Resistance with a Novel ABL Kinase Inhibitor", Science, Jul. 16, 2004, pp. 399-401, vol. 305, No. 5682.
Gumireddy, K. et al. "A non-ATP-competitive inhibitor of BCR-ABL overrides imatinib resistance", PNAS, Feb. 8, 2005, pp. 1992-1997, vol. 102, No. 6.

*Primary Examiner*—Raymond J Henley, III
(74) *Attorney, Agent, or Firm*—Scully, Scott, Murphy & Presser, P.C.

(57) ABSTRACT

The invention provides low molecular weight compounds, namely 1H-thieno[2,3-c]pyrazoles, showing a high affinity for the ATP pocket of ABL tyrosine kinase. These compounds are thus ATP-competitive tyrosine kinase inhibitors displaying a significant inhibitory potency also, and in particular, towards BCR-ABL inhibitor-resistant T315I ABL mutants. The compounds of the invention find a useful application in the treatment of BCR-ABL inhibitor-resistant ABL-mediated diseases, such as Imatinib-resistant chronic myelogenous leukemia. Moreover, the invention provides a screening method for the identification of compounds capable of binding the ATP pocket of a kinase protein, in particular of the T315I mutant ABL kinase.

25 Claims, 3 Drawing Sheets

USE OF A KINASE INHIBITOR FOR THE TREATMENT OF PARTICULAR RESISTANT TUMORS

TECHNICAL FIELD

The present invention relates to the treatment of mutated ABL-mediated diseases through the use of ATP-competitive small molecules kinase inhibitors.

BACKGROUND ART

Chronic Myelogenous Leukemia (CML) is a hematological disorder which constitutes about 15% of adult leukemias, characterized by the malignant expansion of the myeloid lineage. The genetic hallmark of CML is a reciprocal translocation between chromosomes 9 and 22 resulting in the so-called Philadelphia (Ph) chromosome. The molecular consequence of this inter-chromosomal exchange is the creation of the chimeric gene BCR-ABL, encoding a tyrosine kinase polypeptide in which the tyrosine kinase domain is constitutively activated. The expression of this fusion protein has been shown to be necessary and sufficient for the transformed phenotype of CML cells (FADERL, S, et al. The biology of chronic myeloid leukemia. New England Journal of Medicine. 1999, vol. 341, no. 3, p. 164-172. SAWYERS, C. Chronic myeloid leukemia. New England Journal of Medicine. 1999, vol. 340, no. 17, p. 1330-1340.) In addition to CML, deregulated ABL kinase activity resulting from the Ph chromosomal translocation is also detected in up to 20% of adult lymphoblastic leukemia (ALL) patients (OTTMANN, O. G., et al. A phase 2 study of imatinib in patients with relapsed or refractory Philadelphia chromosome-positive acute lymphoid leukemias. Blood. 2002, vol. 100, no. 6, p. 1965-1971.)

ABL transduces signals from cell-surface growth factor and adhesion receptors to regulate cytoskeleton structure. Many signalling proteins have been shown to interact with ABL which activate a range of signalling pathways. Therefore, inhibition of ABL constitutes a new approach to improve therapy for patients with CML.

The discovery that BCR-ABL is required for the pathogenesis of CML, and that the tyrosine kinase activity of ABL is essential for BCR-ABL-mediated transformation, made the ABL kinase an attractive target for therapeutic intervention. Imatinib (Gleevec®, also known as STI571, EP 564409 A) is an ATP-competitive inhibitor of BCR-ABL which potently inhibits its tyrosine kinase activity The high selectivity and efficacy of Imatinib are due to its ability to bind and block BCR-ABL in a catalytically inactive conformation of the enzyme. Preclinical and clinical studies have demonstrated the remarkable efficacy and high tolerability of Imatinib, which is now the first-line treatment for all newly diagnosed CML patients (DEININGER, M, et al. The development of imatinib as a therapeutic agent for chronic myeloid leukemia. Blood. 2005, vol. 105, no. 7, p. 2640-2653.) However, Imatinib is highly effective in early phases of the disease, whereas patients in the accelerated and blastic phase of CML, as well as those with Ph+ ALL, frequently develop Imatinib-resistance (DRUKER, B. J., et al. Activity of a specific inhibitor of the BCR-ABL tyrosine kinase in the blast crisis of chronic myeloid leukemia and acute lymphoblastic leukemia with the Philadelphia chromosome. New England Journal of Medicine. 2001, vol. 344, no. 14, p. 1038-1042. SAWYERS, C. L., et al. Imatinib induces hematologic and cytogenetic responses in patients with chronic myelogenous leukemia in myeloid blast crisis: results of a phase II study. Blood. 2002, vol. 99, no. 10, p. 3530-3539.) A major mechanism for Imatinib-resistance is the evolution of clones that have acquired point mutations within the tyrosine kinase catalytic domain of BCR-ABL and directly prevent or weaken the interaction with the inhibitor. While most of them induce structural changes that prevent the ABL kinase domain to adopt the closed, inactive conformation required for Imatinib binding (SHAH, N. P., et al. Mechanisms of resistance to STI571 in Philadelphia chromosome-associated leukemias. Oncogene. 2003, vol. 22, no. 47, p. 7389-7395.), some mutations, such as the Threonine 315 to Isoleucine substitution (hereinafter referred to as T315I), directly interfere with Imatinib interaction at the ATP binding pocket.

The understanding of the molecular basis of Imatinib resistance has stimulated the search for new BCR-ABL inhibitors that are effective against clinically observed imatinib-resistant ABL-mediated diseases. A number of second generation ATP-competitive inhibitors of BCR-ABL, such as AMN107 (WEISBERG, F, et al. Characterization of AMN107, a selective inhibitor of native and mutant Bcr-Abl. Cancer Cell. 2005, vol. 7, p. 129-141.) and BMS-354825 (also known as Desatinib) (SHAH, N. P., et al. Overriding imatinib resistance with a novel ABL kinase inhibitor. Science. 2004, vol. 305, no. 5682, p. 399-401.), have been developed and are now under evaluation in early clinical trials. These compounds are active against the majority of the Imatinib-resistant ABL mutants, but none of them is active against the T315I mutant, which is the second most frequent mutation occurring in Imatinib-resistance patients (O'HARE, T, et al. In vitro activity of Bcr-Abl inhibitors AMN107 and BMS-354825 against clinically relevant imatinib-resistant Abl kinase domain mutants. Cancer Research. 2005, vol. 65, no. 11, p. 4500-4505). It can be concluded that it is particularly difficult to inhibit the T315I ABL mutation with an ATP-competitive compound. As a matter of fact, until very recently the only inhibitor that has been reported to be active also against the T315I mutant was ON12380, which indeed is a substrate competitive (i.e. a non-ATP competitive) inhibitor (GUMIREDDY, K., et al. A non-ATP-competitive inhibitor of BCR-ABL overrides imatinib resistance. Proc. Natl. Acad. Sci. U.S.A. . 2005, vol. 102, no. 6, p. 1992-1997.).

Recently, two ATP-competitive molecules, VX-680 (HARRINGTON, E. A., et al. VX-680, a potent and selective small-molecule inhibitor of the Aurora kinases, suppresses tumor growth in vivo. Nature Medicine. 2004, vol. 10, no. 3, p. 262-267.) and BIRB-796 (PARGELLIS, C., et al. Inhibition of p38 MAP kinase by utilizing a novel allosteric binding site. Nat. Struct. Biol. 2002, vol. 9, no. 4, p. 268-272.) have been reported to be able to bind in vitro to the T315I mutated tyrosine kinase domain of ABL with low nanomolar Kd, but showed a low potency for inibition of T315I BCR-ABL in cells (CARTER, T. A., et al. Inhibition of drug-resistant mutants of ABL, KIT, and EGF receptor kinases. Proc. Natl. Acad. Sci. U.S.A. 2005, vol. 102, no. 31, p. 11011-11016).

At present, there are no effective kinase-targeted treatments for patients affected by Imatinib-resistant T315I ABL-mediated diseases, which are estimated to constitute 20% of all patients that relapse after imatinib treatment and are expected to be selected for by treatment with the next generation inhibitors mentioned above. This represents an unmet medical need for new potent ATP-competitive inhibitor of the T315I mutant of BCR-ABL. The present invention addresses this problem.

SUMMARY OF THE INVENTION

The invention provides low molecular weight compounds showing a high affinity for the ATP pocket of ABL tyrosine kinase. These compounds are thus ATP-competitive tyrosine kinase inhibitors displaying a significant inhibitory potency towards BCR-ABL inhibitor-resistant T315I ABL mutants, in particular towards Imatinib-resistant T315I ABL mutants. Inhibition of the tyrosine kinase activity results in the block of the signalling cascade mediated by ABL and the T315I mutant.

The compounds of the present invention showing the desired activity are 1H-thieno[2,3-c]pyrazoles designed to target the ATP pocket of protein kinases. Compounds of this chemical class have revealed to be potent ATP-competitive inhibitors of Aurora kinases (PCT/WO 2005074922). Unexpectedly, compounds with the same chemical scaffold have been found to display a significant inhibitory potency towards ABL and in particular they are able to inhibit in vitro also BCR-ABL inhibitor-resistant T315I mutant form of ABL.

In view of their biological activity, the compounds of the invention offer a new path for the development of a treatment for Imatinib-resistant patient population suffering from ABL-mediated diseases.

The invention also provides an assay for the identification of additional compounds that bind the ATP pocket of a target protein kinase, in particular ABL tyrosine kinase. This assay relies on the ability to detect the result of the binding to the target ATP pocket and it is conducted in quantitative conditions so that the binding affinity of a compound to the ATP pocket can be determined.

DETAILED DESCRIPTION OF THE INVENTION

In a first aspect, the present invention relates to a method for inhibiting a BCR-ABL inhibitor-resistant tyrosine kinase activity comprising contacting a BCR-ABL inhibitor-resistant tyrosine kinase polypeptide with an effective amount of the compound of formula (I)

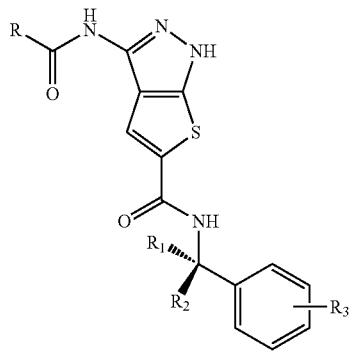

(I)

wherein R is an optionally substituted aryl or heteroaryl group;

$R_1$ and $R_2$ represent, the same or different and independently from each other, a hydrogen atom, a straight or branched $C_1$-$C_3$ alkyl or, taken together with the carbon atom to which they are bonded, $R_1$ and $R_2$ may form a $C_3$-$C_6$ cycloalkyl group; with the proviso that at least one of $R_1$ and $R_2$ is other than a hydrogen atom;

$R_3$ is a hydrogen or halogen atom or a group selected from hydroxy, cyano, straight or branched $C_1$-$C_3$ alkyl or $C_1$-$C_3$ alkoxy.

The compounds of formula (I) of the invention have asymmetric carbon atoms and may therefore exist as individual optical isomers, as racemic mixtures or as any other mixture comprising a majority of one of the two optical isomers, which are all to be intended as within the scope of the present invention.

In cases when compounds may exist in tautomeric forms, each form is contemplated as being included within this invention whether existing in equilibrium or predominantly in one form.

As such, unless otherwise provided, when only one of the following tautomeric forms of formula (Ia) or (Ib) is indicated, the remaining one has still to be intended as comprised within the scope of the invention:

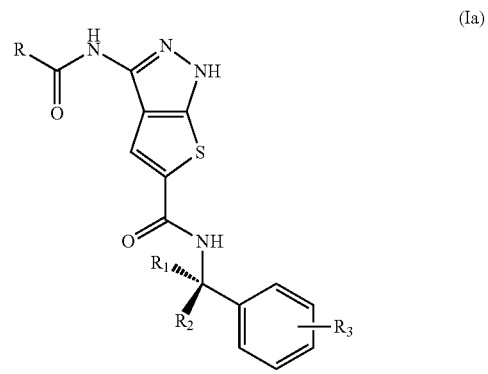

(Ia)

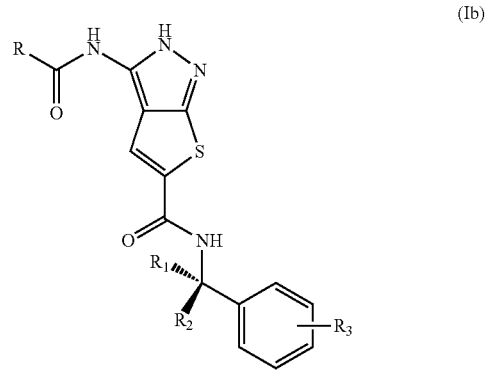

(Ib)

In the present description, unless otherwise specified, with the term aryl group we intend any aromatic carbocyclic ring system of 1 or 2 ring moieties, either fused or linked to each other through a single bond, for instance including phenyl, a- or b-naphthyl or biphenyl groups.

With the term heteroaryl we intend any aromatic heterocyclic ring which may comprise an optionally benzocondensed 5 or 6 membered heterocycle with from 1 to 3 heteroatoms selected among N, O or S.

Non limiting examples of heteroaryl groups according to the invention may thus include, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, and the like.

With the term straight or branched $C_1$-$C_3$ alkyl or $C_1$-$C_3$ alkoxy we intend any of the groups such as methyl, ethyl, n-propyl, isopropyl, methoxy, ethoxy, n-propoxy and isopropoxy.

With the term halogen atom we intend a fluorine, chlorine, bromine or iodine atom.

With the term $C_3$-$C_6$ cycloalkyl we intend any group such as cyclopropyl, cyclobutyl, cyclopentyl and cyclohexyl.

Clearly, as these same cycloalkyl groups may be formed when $R_1$ and $R_2$ are taken together with the carbon atom to which they are attached, cyclic spiro compounds may be thus obtained.

Clearly, as these same cycloalkyl groups may be formed when $R_1$ and $R_2$ are taken together with the carbon atom to which they are attached, cyclic spiro compounds may be thus obtained. Just as an example, when $R_1$ and $R_2$ together form a cyclopentyl group, derivatives having the following general formula are herewith considered:

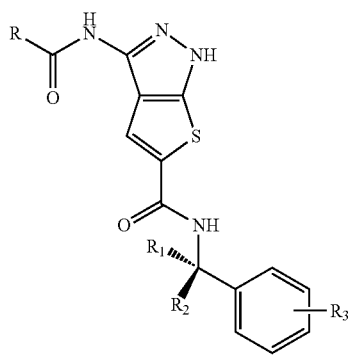

When considering derivatives of formula (I) wherein $R_1$ or $R_2$ represents a group
—$CH_2NR'R''$ and $R'$ and $R''$ are linked together with the nitrogen atom to which they are attached, heterocyclic moieties may be thus formed as per the general formula. Just as an example, by considering $R_1$ as hydrogen and $R_2$ as a group —$CH_2NR'R''$ with $R'$ and $R''$ linked together so as to form a pyrrolidinyl-1-yl group, compounds having the following general formula formula are herewith considered:

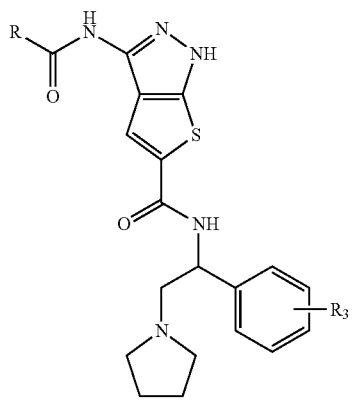

From all of the above, it is clear to the skilled man that the compounds of formula (I) of the invention are characterized by the presence of a moiety, hereinafter simply referred to as benzylamino moiety, wherein the methylene group is necessarily substituted by at least one of the groups $R_1$ and $R_2$ which is different from hydrogen.

According to the meanings provided to R, any of the above aryl or heteroaryl groups may be optionally further substituted in any of their free positions by one or more groups, for instance 1 to 6 groups, selected from: halogen, nitro, oxo groups (=O), carboxy, cyano, alkyl, polyfluorinated alkyl, alkenyl, alkynyl, cycloalkyl, cycloalkenyl; aryl, heterocyclyl, alkyl-heterocyclyl, heterocyclyl-alkyl, amino groups and derivatives thereof such as, for instance, alkylamino, dialkylamino, arylamino, diarylamino, ureido, alkylureido or arylureido; carbonylamino groups and derivatives thereof such as, for instance, formylamino, alkylcarbonylamino, alkenylcarbonylamino, arylcarbonylamino, alkoxycarbonylamino; hydroxy groups and derivatives thereof such as, for instance, alkoxy, polyfluorinated alkoxy, aryloxy, heterocylyloxy, alkylcarbonyloxy, arylcarbonyloxy, cycloalkenyloxy or alkylideneaminoxy; carbonyl groups and derivatives thereof such as, for instance, alkylcarbonyl, arylcarbonyl, alkoxycarbonyl, aryloxycarbonyl, cycloalkyloxycarbonyl, aminocarbonyl, alkylaminocarbonyl, dialkylaminocarbonyl; sulfurated derivatives such as, for instance, alkylthio, arylthio, alkylsulfonyl, arylsulfonyl, alkylsulfinyl, arylsulfinyl, arylsulfonyloxy, aminosulfonyl, alkylaminosulfonyl or dialkylaminosulfonyl.

In their turn, whenever appropriate, each of the above substituents may be further substituted by one or more of the aforementioned groups.

With the term alkyl or alkoxy group we intend, unless otherwise provided, any straight or branched $C_1$-$C_6$ alkyl or alkoxy group, hence comprehensive of the aforementioned $C_1$-$C_3$ alkyl or alkoxy groups and also comprising n-butyl, iso-butyl, sec-butyl, tert-butyl, n-pentyl, n-hexyl, n-butoxy, iso-butoxy, sec-butoxy, tert-butoxy, n-pentyloxy, n-hexyloxy, and the like.

With the term alkenyl or alkynyl group we intend, unless otherwise provided, any unsaturated straight or branched $C_2$-$C_6$ alkenyl or alkynyl group such as, for instance, vinyl, allyl, 1-propenyl, isopropenyl, 1-, 2- or 3-butenyl, pentenyl, hexenyl, ethynyl, 1- or 2-propynyl, butynyl, pentynyl, hexynyl, and the like.

With the term polyfluorinated alkyl or alkoxy we intend any straight or branched $C_1$-$C_6$ alkyl or alkoxy group as above defined, wherein more than one hydrogen atom is replaced by fluorine atoms such as, for instance, trifluoromethyl, trifluoromethoxy, 2,2,2-trifluoroethyl, 2,2,2-trifluoroethoxy, 1,2-difluoroethyl, 1,1,1,3,3,3-hexafluoropropyl-2-yl, and the like.

With the term heterocycle, heterocyclyl or heterocyclic group we also intend an optionally benzocondensed 4 to 7 membered heterocycle, hence encompassing aromatic heterocyclic groups also known as heteroaryl groups, either saturated or partially unsaturated, with from 1 to 3 heteroatoms selected among N, O and S.

Examples of these 4 or 7 membered heterocyclic groups are, for instance, 1,3-dioxolane, pyran, pyrrolidine, pyrroline, imidazoline, imidazolidine, pyrazolidine, pyrazoline, piperidine, piperazine, morpholine, tetrahydrofuran, hexamethyleneimine, 1,4-hexahydrodiazepine, azetidine, and the like.

With the term cycloalkenyl we intend any of the aforementioned $C_3$-$C_6$ cycloalkyl groups further comprising a double bond such as, for instance, 2-cyclopenten-1-yl, 3-cyclopenten-1-yl, 1-cyclohexen-1-yl, 2-cyclohexen-1-yl, 3-cyclohexen-1-yl, and the like.

From all of the above, it is clear to the skilled man that any group which name has been identified as a composite name such as, for instance, cycloalkylalkyl, arylalkyl, heterocyclylalkyl, alkylthio, aryloxy, arylalkyloxy, alkylcarbonyloxy and the like, has to be intended as conventionally construed from the parts to which they derive. So far, as an example, the term alkoxy-heterocyclyl-alkyl stands for a straight or branched alkyl group substituted by a heterocycle further substituted by alkoxy, wherein alkyl, heterocycle and alkoxy are as above defined. Likewise, the term alkyl-heterocyclyloxy stands for a heterocyclyloxy group further substituted by alkyl.

The compounds of formula (I) are described and claimed in the International patent application WO2005/074922 and can be prepared according to the process disclosed therein.

The method of the present invention may be performed in vitro or in vivo. A full-length tyrosine kinase polypeptide can be used, alternatively, or fragment, portion, or analog thereof can be employed.

More particularly, the inhibiting activity of selected compounds of the invention is determined through a gel-kinase assay. The assay consists of the transfer of radioactivity labelled phosphate moiety by the ABL kinase to a substrate, in the presence of the test compound. Once terminated the reaction, the reaction mixture is loaded on a polyacrylamide gel and radioactivity signal is detected. This inhibition assay is better illustrated in the Example section.

Additionally, the inhibiting activity of selected compounds of the invention is determined in cellular systems. Suitable cells are those where the BCR-ABL chromosomic translocation has naturally occurred, such as human leukaemia cells K-562 and cells transfected with a recombinant construct carrying the T315I ABL mutant gene. Cells are treated with the compounds of the invention and inhibitory activity is detected by immunoblotting as better illustrated in the Example section.

In a preferred embodiment of the invention, the BCR-ABL inhibitor-resistant tyrosine kinase polypeptide is a T315I mutant of ABL tyrosine kinase.

In a more preferred embodiment of the invention, the BCR-ABL inhibitor is Imatinib.

In a second aspect, the present invention relates to a method of treating a BCR-ABL inhibitor-resistant T315I ABL-mediated disease which comprises administering to a mammal in need thereof an effective amount of the compound according of formula (I) as defined above.

Within the scope of the method of treatment claimed in the present invention is the use of all the possible isomers and their admixtures and of both the metabolites and the pharmaceutically acceptable bio-precursors (otherwise referred to as pro-drugs) of the compounds of formula (I). Prodrugs are any covalently bonded compounds, which release the active parent drug, according to formula (I), in vivo.

The two above methods of the invention are preferably performed with a compound of formula (II)

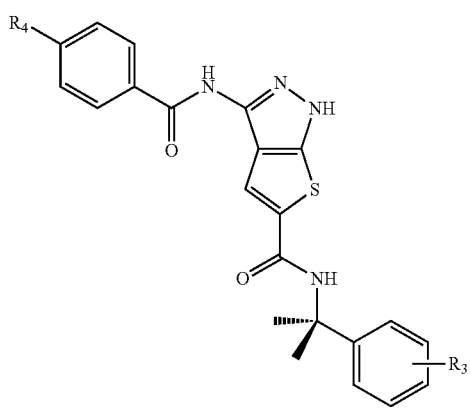

(II)

wherein R$_4$ is a group selected from azetidin-1-yl, pirrolidin-1-yl, piperidin-1-yl, (1-methyl-piperazin-4-yl), (morpholino-4-yl), (azetidin-1-yl)methyl, (pirrolidin-1-yl)methyl, (piperidin-1-yl)methyl, (1-methyl-piperazin-4-yl)methyl, (morpholino-4-yl)methyl, (1-methyl-piperidin-4-yloxy)methyl, (isopropyl amino)methyl; and R$_3$ is a hydrogen or fluorine or chlorine atom.

More preferably, the compounds to be used in the method of the invention are selected from the group consisting of:
N-(1-methyl-1-phenylethyl)-3-[(4-morpholin-4-ylbenzoyl)amino]-1H-thieno[2, 3-c]pyrazole-5-carboxamide;
3-[(4-morpholin-4-ylbenzoyl)amino]-N-(1-phenylcyclopropyl)-1H-thieno[2,3-c]pyrazole-5-carboxamide;
N-(1-methyl-1-phenylethyl)-3-({4-[(1-methylpiperidin-4-yl)oxy]benzoyl}amino)-1H-thieno[2,3-c]pyrazole-5-carboxamide;
3-({4-[(1-methylpiperidin-4-yl)oxy]benzoyl}amino)-N-(1-phenylcyclopropyl)-1H-thieno[2,3-c]pyrazole-5-carboxamide;
N-(1-methyl-1-phenylethyl)-3-({4-[(4-methylpiperazin-1-yl)methyl]benzoyl}amino)-1H-thieno[2,3-c]pyrazole-5-carboxamide;
N-(1-ethyl-1-phenylpropyl)-3-{[4-(4-methylpiperazin-1-yl)benzoyl]amino}-1H-thieno[2,3-c]pyrazole-5-carboxamide;
3-{[(4-(4-methylpiperazin-1-yl)benzoyl]amino}-N-(1-phenylcyclopentyl)-1H-thieno[2,3-c]pyrazole-5-carboxamide;
3-{[4-(4-methylpiperazin-1-yl)benzoyl]amino}-N-(1-phenylcyclopropyl)-1-H-thieno[2,3-c]pyrazole-5-carboxamide;
3-(4-Morpholin-4-yl-benzoylamino)-1H-thieno[2,3-c]pyrazole-5-carboxylic acid (1-ethyl-1-phenyl-propyl)-amide;
3-(4-Morpholin-4-yl-benzoylamino)-1H-thieno[2,3-c]pyrazole-5-carboxylic acid (1-phenyl-cyclopentyl)-amide;
3-[4-(4-Methyl-piperazin-1-yl)-benzoylamino]-1H-thieno[2,3-c]pyrazole-5-carboxylic acid [-(3-chloro-phenyl)-1-methyl-ethyl]-amide;
3-(4-Morpholin-4-ylmethyl-benzoylamino)-1H-thieno[2,3-c]pyrazole-5-carboxylic acid (1-methyl-1-phenyl-ethyl)-amide;
3-(4-Piperidin-1-ylmethyl-benzoylamino)-1H-thieno[2,3-c]pyrazole-5-carboxylic acid (1-methyl-1-phenyl-ethyl)-amide;
3-[4-(Isopropylamino-methyl)-benzoylamino]-1H-thieno[2,3-c]pyrazole-5-carboxylic acid (1-methyl-1-phenyl-ethyl)-amide;
3-(4-Pyrrolidin-1-ylmethyl-benzoylamino)-1H-thieno[2,3-c]pyrazole-5-carboxylic acid (1-methyl-1-phenyl-ethyl)-amide;
3-[4-(4-Methyl-piperazin-1-yl)-benzoylamino]-1H-thieno[2,3-c]pyrazole-5-carboxylic acid [1-(4-fluoro-phenyl)-1-methyl-ethyl]-amide;
3-[4-(4-Methyl-piperazin-1-yl)-benzoylamino]-1H-thieno[2,3-c]pyrazole-5-carboxylic acid [1-(2-fluoro-phenyl)-1-methyl-ethyl]-amide;
3-[4-(4-Methyl-piperazin-1-yl)-benzoylamino]-1H-thieno[2,3-c]pyrazole-5-carboxylic acid [1-(3-fluoro-phenyl)-1-methyl-ethyl]-amide;
3-(4-Morpholin-4-ylmethyl-benzoylamino)-1H-thieno[2,3-c]pyrazole-5-carboxylic acid [1-(3-fluoro-phenyl)-1-methyl-ethyl]-amide;
3-(4-Pyrrolidin-1-ylmethyl-benzoylamino)-1H-thieno[2,3-c]pyrazole-5-carboxylic acid [1-(3-fluoro-phenyl)-1-methyl-ethyl]-amide;

3-(4-Piperidin-1-ylmethyl-benzoylamino)-1H-thieno[2,3-c]pyrazole-5-carboxylic acid [1-(2-fluoro-phenyl)-1-methyl-ethyl]-amide;

3-(4-Azetidin-1-ylmethyl-benzoylamino)-1H-thieno[2,3-c]pyrazole-5-carboxylic acid (1-methyl-1-phenyl-ethyl)-amide;

3-(4-Morpholin-4-yl-benzoylamino)-1H-thieno[2,3-c]pyrazole-5-carboxylic acid [1-(2-fluoro-phenyl)-1-methyl-ethyl]-amide;

3-(4-Morpholin-4-yl-benzoylamino)-1H-thieno[2,3-c]pyrazole-5-carboxylic acid [1-(3-fluoro-phenyl)-1-methyl-ethyl]-amide;

3-(4-Morpholin-4-yl-benzoylamino)-1H-thieno[2,3-c]pyrazole-5-carboxylic acid [1-(4-fluoro-phenyl)-1-methyl-ethyl]-amide;

3-(4-Piperidin-1-ylmethyl-benzoylamino)-1H-thieno[2,3-c]pyrazole-5-carboxylic acid [1-(4-fluoro-phenyl)-1-methyl-ethyl]-amide;

3-(4-Morpholin-4-ylmethyl-benzoylamino)-1H-thieno[2,3-c]pyrazole-5-carboxylic acid [1-(2-fluoro-phenyl)-1-methyl-ethyl]-amide;

3-(4-Morpholin-4-ylmethyl-benzoylamino)-1H-thieno[2,3-c]pyrazole-5-carboxylic acid [1-(4-fluoro-phenyl)-1-methyl-ethyl]-amide;

3-(4-Piperidin-1-ylmethyl-benzoylamino)-1H-thieno[2,3-c]pyrazole-5-carboxylic acid [1-(3-fluoro-phenyl)-1-methyl-ethyl]-amide 3-(4-Azetidin-1-ylmethyl-benzoylamino)-1H-thieno[2,3-c]pyrazole-5-carboxylic acid [1-(2-fluoro-phenyl)-1-methyl-ethyl]-amide;

3-(4-Dimethylaminomethyl-benzoylamino)-1H-thieno[2,3-c]pyrazole-5-carboxylic acid (1-methyl-1-phenyl-ethyl)-amide;

3-(4-Cyclopropylaminomethyl-benzoylamino)-1H-thieno[2,3-c]pyrazole5-carboxylic acid (1-methyl-1-phenyl-ethyl)-amide, 3-(4-Cyclobutylaminomethyl-benzoylamino)-1H-thieno[2,3-c]pyrazole-5-carboxylic acid (1-methyl-1-phenyl-ethyl)-amide;

3-{4[-(Isopropyl-methyl-amino)-methyl]-benzoylamino}-1H-thieno[2,3-c]pyrazole-5-carboxylic acid (1-methyl-1-phenyl-ethyl)-amide;

3-(4-Cyclopentylaminomethyl-benzoylamino)-1H-thieno[2,3-c]pyrazole-5-carboxylic acid (1-methyl-1-phenyl-ethyl)-amide;

3-{4-[(Diisopropylamino)-methyl]-benzoylamino}-1H-thieno[2,3-c]pyrazole-5-carboxylic acid (1-methyl-1-phenyl-ethyl)-amide;

3-(4-Pyrrolidin-1-ylmethyl-benzoylamino)-1H-thieno[2,3-c]pyrazole-5-carboxylic acid [1-(2-fluoro-phenyl)-1-methyl-ethyl]-amide;

3-[4-(4-Methyl-piperazin-1-yl)-benzoylamino]-1H-thieno[2,3-c]pyrazole-5-carboxylic acid [1-methyl-1-(2-fluorophenyl)-ethyl]-amide;

3-{(4-[(1-methylpiperidin-4-yl)oxy]benzoyl}amino)-1H-thieno[2,3-c]pyrazole-5-carboxylic acid [1-methyl-1-(2-fluoro-phenyl)-ethyl]-amide;

3-(4-Cyclopropylaminomethyl-benzoylamino)-1H-thieno[2,3-c]pyrazole-5-carboxylic acid 1-(2-fluoro-phenyl)-1-methyl-ethyl]-amide;

3-[4-(Isopropylamino-methyl)-benzoylamino]-1H-thieno[2,3-c]pyrazole-5-carboxylic acid 1-(2-fluoro-phenyl)-1-methyl-ethyl]-amide;

3-Benzoylamino-1H-thieno[2,3-c]pyrazole-5-carboxylic acid (1-methyl-1-phenyl-ethyl)-amide;

3-(4-Azepan-1-ylmethyl-benzoylamino)-1H-thieno[2,3-c]pyrazole-5-carboxylic acid (1-methyl-1-phenyl-ethyl)-amide;

3-(4-Azepan-1-ylmethyl-benzoylamino)-1H-thieno[2,3-c]pyrazole-5-carboxylic acid [1-(2-fluoro-phenyl)-1-methyl-ethyl]-amide A most preferred subset of compounds to be used in the method of the invention is the one consisting of:

N-(1-methyl-1-phenylethyl)-3-({4-[(1-methylpiperidin-4-yl)oxy]benzoyl}amino)-1H-thieno[2,3-c]pyrazole-5-carboxamide;

3-(4-Piperidin-1-ylmethyl-benzoylamino)-1H-thieno[2,3-c]pyrazole-5-carboxylic acid (1-methyl-1-phenyl-ethyl)-amide;

N-(1-methyl-1-phenylethyl)-3-{4-(4-methylpiperazin-1-yl)benzoylamino}-1H-thieno[2,3-c]pyrazole-5-carboxamide;

N-(1-methyl-1-phenylethyl)-3-({4-[(4-methylpiperazin-1-yl)methyl]benzoyl}amino)-1H-thieno[2,3-c]pyrazole-5-carboxamide;

3-(4-Piperidin-1-ylmethyl-benzoylamino)-1H-thieno[2,3-c]pyrazole-5-carboxylic acid [1-(2-fluoro-phenyl)-1-methyl-ethyl]-amide.

The most preferred compound to be used in the two above methods of the invention is 3-(4-Piperidin-1-ylmethyl-benzoylamino)-1H-thieno[2,3-c]pyrazole-5-carboxylic acid (1-methyl-1-phenyl-ethyl)-amide, herein below referred to as "Compound 1".

Pharmaceutically acceptable salts of the compounds of formula (I) include the acid addition salts with inorganic or organic acids such as, for instance, nitric, hydrochloric, hydrobromic, sulfuric, perchloric, phosphoric, acetic, trifluoroacetic propionic, glycolic, lactic, oxalic, malonic, malic, maleic, tartaric, citric, benzoic, cinnamic, mandelic, methanesulphonic, isethionic and salicylic acid.

The term "T315I ABL-mediated disease" is intended to encompass diseases in which, directly or indirectly, inhibiting the activity of T315I ABL tyrosine kinase is desirable.

The term "BCR-ABL inhibitor" is intended to encompass ATP-competitive molecules having the ability of inhibiting the enzymatic activity of the BCR-ABL protein. Non-limiting examples of such molecules are Imatinib, Desatinib and AMN107.

In a preferred embodiment of the method described above, the disease is a BCR-ABL inhibitor-resistant leukaemia caused by the T315I mutant of ABL tyrosine kinase. In a more preferred embodiment the leukaemia is chronic myelogenous leukaemia.

In another preferred embodiment of the method described above, the BCR-ABL inhibitor is Imatinib.

A compound according to formula (I) may be administered to a subject upon determination of the subject as having a disease or unwanted condition that would benefit by treatment with said compound. Medical or clinical personnel may make the determination as part of a diagnosis of a disease or condition in a subject. The compound may also be used in the prevention of such conditions, which may be viewed as reducing the probability of a subject having one or more of the conditions.

The method of the invention can be performed by contacting a cell with a compound of formula (I) that inhibits one or more of the activities of the T315I ABL mutant. This method can be performed in vitro (e.g., by culturing the cell with the compound) or, alternatively, in vivo (e.g. by administering the compound to a subject). It may also be performed ex vivo, as in the case of cells obtained from a subject and treated in vitro followed by their return to the subject.

In vivo, the effect of a target protein inhibiting therapeutic composition can be evaluated in a suitable animal model.

As used herein, an effective amount of a compound refers to an amount sufficient to achieve its intended purpose. Determination of the effective amounts is well within the capability of those skilled in the art based upon the achievement of a desired effect. An effective amount will depend on factors including, but not limited to, the size of a subject and/or the degree to which the disease or unwanted condition from which a subject suffers has progressed. The effective amount will also depend on whether the compound is administered to the subject in a single dosage or periodically over time.

The compounds of formula (I) of the present invention are intended for the treatment of subjects. As used herein, the term "subject" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs and cats; laboratory animals including rodents, such as rats, mice and guinea pigs, and the like. Examples of non-mammals include, but are not limited to, birds, fish and the like.

The term "treating" as used herein includes achieving a therapeutic benefit. By therapeutic benefit is meant eradication or amelioration of the underlying disorder being treated. For example, in a cancer patient, therapeutic benefit includes eradication or amelioration of the underlying cancer. Also, a therapeutic benefit is achieved with the eradication or amelioration of one or more of the physiological symptoms associated with the underlying disorder such that an improvement is observed in the patient, notwithstanding the fact that the patient may still be afflicted with the underlying disorder.

The method of the invention comprises the administration of a compound of formula (I) as a single agent or, alternatively, in combination with one or more other molecule or other agents suitable for treatment of a disease or unwanted condition as disclosed herein. Exemplary molecules and agents suitable for combined treatment are cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose, saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine, methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions or suspensions.

As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier. Intravenous infusions may be carried out in a time interval of from about 1 hour to about 10 hours, following a weekly regimen of treatment for 1 to 6-week cycles.

The suppositories may contain, together with the active compound, a pharmaceutically acceptable carrier, e.g., cocoa butter, polyethylene glycol, a polyoxyethylene sorbitan fatty acid ester surfactant or lecithin.

Pharmaceutical compositions suitable for use in the present invention include compositions wherein the active ingredients are present in an effective amount, i.e., in an amount effective to achieve therapeutic and/or prophylactic benefit in a condition being treated. The actual amount effective for a particular application will depend on the condition or conditions being treated, the condition of the subject, the formulation, and the route of administration, as well as other factors known to those of skill in the art. Determination of an effective amount of the compounds of the present invention is well within the capabilities of those skilled in the art, in light of the disclosure herein, and will be determined using routine optimization techniques.

In therapeutic use, the compounds of the invention are administered to a subject at dosage levels of from about 30 $mg/m^2$ to about 3000 $mg/m^2$ of body surface per day. A dosage level of from about 100 $mg/m^2$ to 1000 $mg/m^2$ constitutes a particularly suitable range. For an adult human subject, a dosage of from about 50 mg to about 5000 mg per dose, more preferably from about 150 mg to about 1000 mg per dose, from 1 to 5 times daily, may be used as a non-limiting example. Lower or higher doses than those disclosed herein may be used, as required. Such dosages, however, may be altered depending on a number of variables, not limited to the activity of the compound used, the condition to be treated, the mode of administration, the requirements of the individual subject, the severity of the condition being treated and the judgment of the practitioner. The foregoing ranges are merely suggestive, as the number of variables in regard to an individual treatment regime is large, and considerable excursions from these recommended values are not uncommon.

The effective amount for use in humans can be determined from animal models. For example, a dose for humans can be formulated to achieve circulating, liver, topical and/or gastrointestinal concentrations that have been found to be effective in animals.

In a third aspect, the present invention relates to a screening method for the identification of compounds capable of binding the ATP pocket of a kinase protein, comprising the steps of:

providing a reaction mixture comprising
the kinase protein,
an indolinone derivative having affinity for the ATP pocket of the said kinase protein and capable of generating a fluorescent signal upon binding to the said ATP pocket, and
serial dilutions of the test compound,
comparing the fluorescent signal generated in the absence of the test compound with the fluorescent signal generated in the presence of different concentrations of the test compound, whereby a decreased level of fluorescence indicates the ability of the test compound to displace the indolinone derivative.

In a preferred embodiment of the screening method, the kinase protein and the indolinone derivative are pre-mixed.

In another preferred embodiment of the screening method, the kinase protein and the test compound are pre-mixed.

In a further preferred embodiment of the screening method, the kinase protein is an ABL kinase. In a more preferred embodiment, the ABL kinase is T315I mutant ABL kinase.

The term "kinase protein" encompasses full-length native proteins as well as fragments thereof, insofar as the fragment comprises the ATP pocket of the kinase protein.

The term "ATP pocket" indicates the ATP binding site within the kinase protein.

The indolinone derivative is preferably a compound of formula (III) below

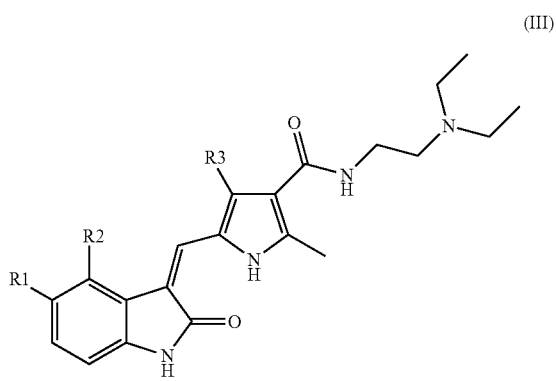

(III)

wherein R1 is hydrogen or methylamino-sulfonyl or benzyl-sulfonyl, R2 is hydrogen or methyl, R3 is methyl or 4-chlorophenyl or 2,4-difluorophenyl.

More preferably, the indolinone derivative is a compound selected from the group consisting of: 2,4-dimethyl-5-[2-oxo-5-phenylmethanesulfonyl-1,2-dihydro-indol-(3Z)-ylidenemethyl]-1H-pyrrole-3-carboxylic acid (2-diethylamino-ethyl)-amide (which has been disclosed in International patent application WO02/096361);

4-(4-chlorophenyl)-N-[2-(diethylamino)ethyl]-2-methyl-5-((Z)-{5-[(methylamino)sulfonyl]-2-oxo-1,2-dihydro-3H-indol-3-ylidene}methyl)-1H-pyrrole-3-carboxamide;

N-[2-(diethylamino)ethyl]-4-(2,4-difluorophenyl)-2-methyl-5-((Z)-{5-[(methylamino)sulfonyl]-2-oxo-1,2-dihydro-3H-indol-3-ylidene}methyl)-1H-pyrrole-3-carboxamide;

4-(4-chlorophenyl)-N-[2-(diethylamino)ethyl]-2-methyl-5-[(Z)-(4-methyl-2-oxo-1,2-dihydro-3H-indol-3-ylidene)methyl]-1H-pyrrole-3-carboxamide.

The indolinone derivatives were selected for their capability of binding to the ATP-pocket of both wild type and mutated forms of ABL, for the affinity of the probe for the kinase protein, for the assay robustness, and agreement with published data on known ABL inhibitors (eg: Imatinib).

The fluorescence signal can be measured, e.g., by a plate reader such as the Fusion α-FP HT plate reader (Packard). The displacement ability of the test compound is in direct correlation with the compound affinity for the ATP pocket of the kinase protein. Affinity binding constant (KD) of the test compound can be determined as explained in the Example section.

The assay of the invention is based on the new finding that a significant increase in fluorescence intensity is observed upon binding of indolinone derivatives to kinase proteins. So far, groups chemically linked to an affinity probe capable of binding the target moiety provided for the fluorescent signal. However, such methods suffered from disadvantages related to the low affinity for the kinase pocket that hampered the possibility to set up sensitive assays. An alternative approach that has been used relies on immobilized probe ligand or kinase protein with the typical limitations of a solid phase assay (e.g. stric hindrance and need for washes).

The present invention overcomes these drawbacks, since indolinones show a relatively high affinity for the target kinase and the signal generated upon binding is directly dependent on the binding, allowing to build a homogeneous assay.

Whereas the present screening assay is hereby exemplified with the ABL kinase, the expert in the art will be able to perform it, without undue experimentation, also with other kinase proteins, provided the kinase protein contains an ATP pocket. Indeed, the present inventors have been able to detect a change in the fluorescence signal when the assay is performed with Insulin-like Growth Factor(unphosphorylated and tri-phosphorylated) Insulin Receptor (unphosphorylated and tri-phosphorylated), c-Met, Alk, Chk1 and PDK1. It is therefore expected that further protein kinases can be suitably employed in the assay of the present invention.

Finally, the present invention relates to the use of the compound of formula (I) or a pharmaceutically acceptable salt thereof, as defined above, in the manufacture of a medicamenifor treating a BCR-ABL inhibitor-resistant T315I ABL-mediated disease.

With the aim to better illustrate the present invention, without posing any limitation to it, the following examples are now given.

EXAMPLES

Figure 1:
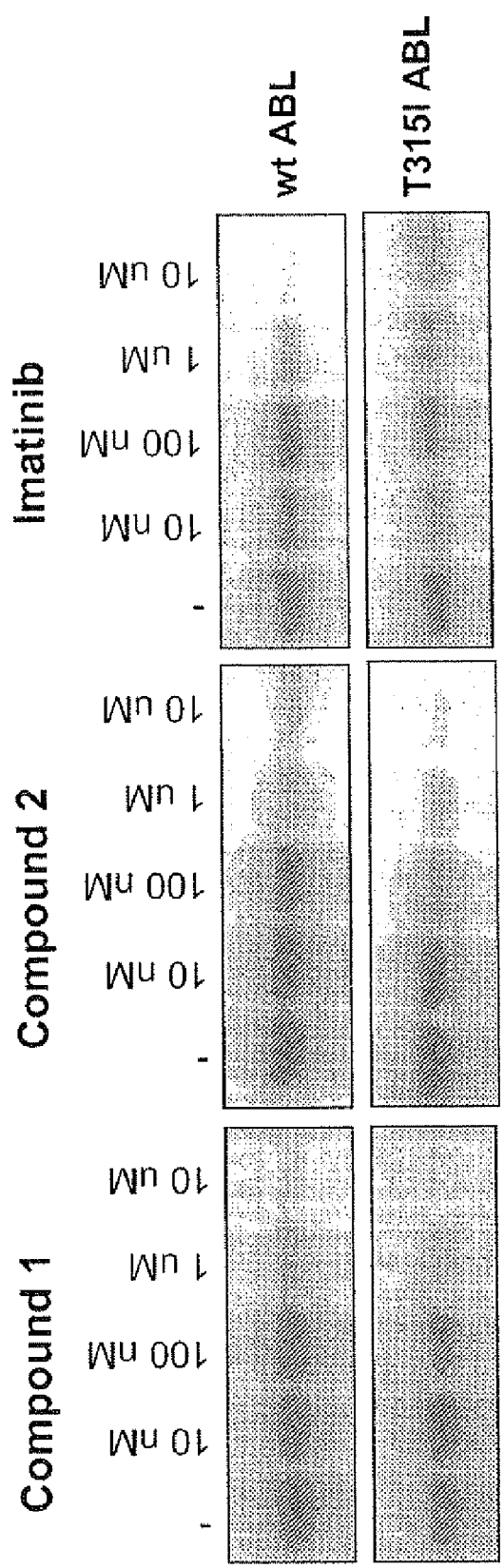
FIG. 1 illustrates the inhibitory activity of Compound 1, 3-(4-Piperidin-1-ylmethyl-benzoylamino)-1H-thieno[2,3-c]pyrazole-5-carboxylic acid [1-(2-fluoro-phenyl)-1-methyl-ethyl]-amide (Compound 2) and of Imatinib on the kinase activity of wild-type ABL and T315I ABL mutant kinase domains. The inhibitory activity was measured by gel kinase assay in the presence of increasing concentration of the compound. Myelin Basic Protein was used as substrate.

In the following examples, numbers of the amino acid residues refer to the Genbank accession number for the isoform 1a of the ABL protein AAB60394

Example 1

Cloning, Expression and Purification of Recombinant Abl Kinase Domains

ABL kinase domain (corresponding to residues 229-512) was PCR amplified from a human testis cDNA library. Amplification was performed using the forward oligonucleotide:

```
                                            [SEQ ID NO: 1]
5'GGGGACAAGTTTGTACAAAAAAGCAGGCTTACTGGAAGTTCTGTTCCA
GGGGCCCTCCCCCAACTACGACAAGTG-3'
and the reverse oligonucleotide:

[SEQ ID NO: 2]
5'GGGGACCACTTTGTACAAGAAAGCTGGGTTTTATTTCCCCAGCTCCTT
TTCCAC-3'
```

For cloning purposes, the oligonucleotides included attB sites in order to obtain an attb-flanked PCR product suitable for cloning using the Gateway® technology (Invitrogen). Furthermore, for purification purposes, forward primer included a PreScission® cleavage site (Amersham Biosciences). The resulting PCR product was cloned in the baculovirus expression vector pVL1393 (Invitrogen) Gateway®-modified. For expression and purification purposes, a GST tag was added N-terminal to the ABL kinase domain. Cloning was performed according to the protocols described in the Gateway® manual.

The Imatinib-resistant T315I ABL mutant was generated by site-directed mutagenesis using the QuikChange® mutagenesis kit (Stratagene). Oligonucleotide used in the mutagenesis reaction was:

```
                                            [SEQ ID NO: 3]
5'-CCCCGTTCTATATCATCATTGAGTTCATGACCTACG-3'.
```

Baculoviruses were generated by cotransfecting Sf9 insect cells with the expression vector and the viral DNA using the BaculoGold® transfection kit (Pharmingen). Viral supernatants were recovered after 5 days and subjected to 3 rounds of amplification to increase viral titer. Recombinant proteins were produced by infecting High5 insect cells at the density of $1\times10^6$ cells per ml with 3 ml viral supernatant per billion cells. After 48 hours of infection, cells were recovered, pelletted and freezed at −80° C. For purification of recombinant proteins, pellets were thawed, resuspended in lysis buffer (Tris-HCl 50 mM, NaCl 150 mM, CHAPS 0.2%, DTT 20 mM, glycerol 10%) and lysed by sonication. Lysates were cleared by centrifugation at 20000 g for 30 minutes and loaded on a Glutathione Sepharose 4B® (Amersham Biosciences) column. After extensive wash, recombinant proteins were cleaved and eluted by incubation with PreScission® protease.

Example 2

Kinase Assay

Activity of compounds was evaluated in a gel-kinase assay that measures phosphorylation of myelin basic protein by recombinant wild-type and T315I mutant ABL kinase domains. Kinase assays were performed in a 20 μl of a reaction mixture containing 15 nM of recombinant enzyme, 10 μM of Myelin Basic Protein (Sigma-Aldrich) as substrate, 10 mM Hepes pH 7.5, 5 mM $MgCl_2$, 1 mM $MnCl_2$, 1 mM DTT, 15 nM $Na_3VO_4$, 4% DMSO, 3 nM ATP, 0.1 μCurie of $\gamma P^{32}$-ATP. Compound 1 and Compound 2 as defined above were tested and Imatinib was also tested in parallel as reference. The inhibitor concentration ranged from 10 nM to 10 μM. After preincubating enzyme and substrate with the inhibitor for 15 minutes at room temperature, ATP was added and reaction was carried on for 30 minutes at 30° C. and terminated with addition of get loading buffer and boiling for 5 minutes. Reaction mixtures were then loaded on a 10% SDS-polyacrilammide gel. After separation, gels were dried and radioactivity signal was revealed using the PhosphorImager system (Molecular Dynamics).

As expected, Imatinib was able to inhibit the kinase activity only of the wild-type ABL kinase domain, while it was completely inactive on the T315I mutant. On the contrary, the two compounds tested were active on both the wild-type and the T315I mutant with the same potency.

Example 3

ATP Site-dependent Displacement Assay Set-up and Validation

An ATP-site dependent displacement assay was set-up for the quantitative affinity evaluation of the tested compounds.

The assay takes advantage of the significant increase in fluorescence intensity observed upon binding of indolinones to kinase proteins. Here below, we show the results obtained with two different indolinones, selected as potential probes on the basis of the magnitude of fluorescence increase upon binding to ABL.

3.1 Indolinone probe 2,4-dimethyl-5-[2-oxo-5-phenylmethanesulfonyl-1,2-dihydro-indol-(3Z)-ylidenemethyl]-1H-pyrrole-3-carboxylic acid (2-diethylamino-ethyl)-amide Indolinone 2,4-dimethyl-5-[2-oxo-5-phenylmethanesulfonyl-1,2-dihydro-indol-(3Z)-ylidenemethyl]-1H-pyrrole-3-carboxylic acid (2-diethylamino-ethyl)-amide was evaluated for its ability to bind the wild-type ABL kinase domain and the T315I ABL mutant in a titration experiment. The assay performance (Z' factor) as well as the displacement of the probe by ATPγS and Imatinib were evaluated. In all experiments, the fluorescence signal was measured using a Fusion α-FP HT plate reader (Packard). Data analysis was performed using the Dynafit software.

In particular, titration data were fitted to the following equilibria: Enzyme+probe<==>Complex Enzyme–probe, while displacement data were fitted to the following equilibria: Enzyme+probe <==>Complex Enzyme-probe, Enzyme+Compound<==>Complex Enzyme-Compound, whereby binding of probe and compound on the enzyme are mutually exclusive (pure competitive mechanism).

The titration experiment was performed as follows: 10 nM ABL kinase domains (wild-type or T315I mutant), indolinone concentration from 3 μM to 0, with dilution steps 1:1.5 in 50 mM TrisHCl, pH 7.5, 150 mM NaCl, 5 mM MgCl$_2$, 1 mM MnCl$_2$, 1 mM DTT, 1% DMSO, 3 μM NaaVO$_4$ (buffer 1). The obtained results (shown in Table 1 below) indicate that the probe is capable of binding all of the tested forms of ABL kinase domain. The Z' factor (Z'=1−(3*(SD$_{probe+protein}$+SD$_{probe}$)/(Mean$_{probe+protein}$−Mean$_{probe}$)) was determined as follow: saturating probe concentration (0.15, 0.12 and 0.42 μM for ABL wild-type unphosphorylated (0P), wild-type and T315I, respectively) were evaluated in the presence (probe+protein) or in the absence (probe) of 10 and 5 nM protein. In all cases, the Z' were greater than 0.8 indicating that the assays were robust.

The assay was validated using ATPγS and Imatinib in a displacement assay performed as follows: serial dilutions of test compounds (dilution steps 1:2) were first prepared in 7% DMSO and further diluted in assay buffer 1 in order to have a 1% final DMSO concentration. ATPγS was tested at 250 μM as highest concentration, while 10 μM was Imatinib highest concentration. The enzymes were present at a final concentration of 10 nM. Probe final concentrations were 0.15, 0.12 and 0.42 μM respectively for ABL wild-type unphosphorylated (0P), wild-type and T315I, respectively. The mixture of enzyme and probe was added to the previously diluted compounds. Results (Table 1) indicates that the probe could be fully displaced by ATPγS from all of the tested ABL constructs indicating that the indolinone binds in the ATP pocket. In agreement, affinity binding constants (KD) were determined by fitting with a pure competitive mechanism. KD values, are the average of three independent experiments.

Imatinib, as expected, showed a higher affinity for the unphosphorylated rather than for the phosphorylated form of ABL, whereas no displacement was observed on the T315I ABL mutant.

TABLE 1

|  | Wild-type ABL 0P | Wild-type ABL | T315I ABL |
| --- | --- | --- | --- |
| Probe titration, KD (μM) | 0.05 ± 0.03 | 0.04 ± 0.02 | 0.14 ± 0.07 |
| ATPγS, KD' (μM) | 9.5 ± 3.4 (100% displ.) | 9 ± 1.9 (100% displ.) | 2 ± 0.21 (100% displ.) |
| Imatinib, KD' (μM) | 0.022 ± 0.003 (100% displ.) | 0.17 ± 0.02 (100% displ.) | 0% displ. |

Taken together, these results show that the displacement assay is ATP site-dependent and the measured affinities are in line with published data on Imatinib (CARTER, T. A., et al. Inhibition of drug-resistant mutants of ABL, KIT, and EGF receptor kinases. Proc. Natl. Acad. Sci. U.S.A. 2005, vol. 102, no. 31, p. 11011-11016. FABIAN, Miles A., et al. A small molecule-kinase interaction map for clinical kinase inhibitors. Nat. biotechnol. 2005, vol. 23, no. 3, p, 329-336.) ATP site-dependent displacement assay with recombinant ABL kinase domains.

Compound binding affinity with recombinant wild-type and T315I mutant ABL kinase domains was evaluated in the displacement assay. Compounds of the iso-thienopyrazole chemical class were tested, with Imatinib included for comparison.

Table 2 shows the affinity binding constant determination (KD) for different ABL constructs. VX-680 is an ATP-competitive tyrosine kinase inhibitor from Vertex which has been recently reported to possess in vitro binding ability for T315I ABL mutant; Compounds 1 and 2 as defined above and Compound 3, namely 3-(4-Morpholin-4-ylmethyl-benzoylamino)-1H-thieno[2,3-c]pyrazole-5-carboxylic acid [1-(2-fluoro-phenyl)-1-methyl-ethyl]-amide, are exemplary compounds of the invention.

TABLE 2

|  | Wild-type ABL 0P KD (μM) | Wild-type ABL KD (μM) | T315I ABL KD (μM) |
| --- | --- | --- | --- |
| VX 680 (Vertex) | 0.032 ± 0.007 | 0.031 ± 0.007 | 0.027 ± 0.001 |
| Compound 1 | 0.24 ± 0.03 | 0.25 ± 0.075 | 0.021 ± 0.006 |
| Compound 2 | 0.107 ± 0.021 | 0.177 ± 0.032 | 0.015 ± 0.004 |
| Compound 3 | 0.33 ± 0.15 | 0.37 ± 0.16 | 0.047 ± 0.015 |
| Imatinib | 0.022 ± 0.003 | 0.117 ± 0.02 | 0% displ. |

Affinity binding constant (KD) towards T315I ABL mutant was also determined for additional exemplary compounds of the invention. Results are reported below in Table 3, wherein Compound 4 is 3-[4-(1-Methyl-piperidin-4-yloxy)-benzoylamino]-1H-thieno[2,3-c]pyrazole-5-carboxylic acid (1-methyl-1-phenyl-ethyl)-amide, Compound 5 is 3-[4-(4-Methyl-piperazin-1-yl)-benzoylamino]-1H-thieno[2,3-c]pyrazole-5-carboxylic acid (1-methyl-1-phenyl-ethyl)-amide, Compound6 is 3-(4-Piperidin-1-ylmethyl-benzoylamino)-1H-thieno[2,3-c]pyrazole-5-carboxylic acid [1-(4-fluoro-phenyl)-1-methyl-ethyl]-amide, Compound 7 is 3-[4-(Iso-propylamino-methyl)-benzoylamino]-1H-thieno[2,3-c]pyrazole-5-carboxylic acid [1-(2-fluoro-phenyl)-1-methyl-ethyl-amide, Compound 8 is 3-[4-(4-Methyl-piperazin-1-yl)-benzoylamino)-1H-thieno[2,3-c]pyrazole-5-carboxylic acid [1-(2-fluoro-phenyl)-1-methyl-ethyl]-amide, Compound 9 is 3-(4-Piperidin-1-ylmethyl-benzoylamino)-1H-thieno[2,3-c]pyrazole-5-carboxylic acid [1-(2-chloro-phenyl)-1-methyl-ethyl]-amide, Compound 10 is 3-[4-(4-Methyl-piperazin-1-ylmethyl)-benzoylamino]-1H-thieno[2,3-c]pyrazole-5-carboxylic acid (1-methyl-1-phenyl-ethyl)-amide, Compound 11 is 3-[4-(Isopropylamino-methyl)benzoylamino)-1H-thieno[2,3-c]pyrazole-5-carboxylic acid (1-methyl-1-phenyl-ethyl)-amide, Compound 12 is 3-(4-Morpholin-4-yl-benzoylamino)-1H-thieno[2,3-c]pyrazole-5-carboxylic acid (1-methyl-1-phenyl-ethyl)-amide, Compound 13 is 3-(4-Piperidin-1-ylmethyl-benzoylamino)-1H-thieno[2,3-c]pyrazole-5-carboxylic acid [1-(3-fluoro-phenyl)-1-methyl-ethyl]-amide.

TABLE 3

|  | T315I ABL mutant KD (μM) |
| --- | --- |
| Compound 4 | 0.006 ± 0.003 |
| Compound 5 | 0.0041 ± 0.002 |
| Compound 6 | 0.014 ± 0.005 |
| Compound 7 | 0.02 ± 0.002 |
| Compound 8 | 0.012 ± 0.006 |
| Compound 9 | 0.014 ± 0.0035 |
| Compound 10 | 0.0084 ± 0.004 |
| Compound 11 | 0.012 ± 0.0025 |
| Compound 12 | 0.016 ± 0.0037 |
| Compound 13 | 0.01 ± 0.0046 |
| Imatinib | 0% displ. |

The displacement assay was performed as described before, with 3 μM as the highest inhibitor concentration tested. Results showed in tables 2 and 3 indicate that all of the tested compounds were active on the T315I ABL mutant.

3.2 Indolinone probe N-[2-(diethylamino)ethyl]-4-(2,4-difluorophenyl)-2-methyl-5-((Z)-{5-[(methylamino)sulfonyl]-2-oxo-1,2-dihydro-3H-indol-3-ylidene}methyl)-1H-pyrrole-3-carboxamide Indolinone N-[2-(diethylamino)ethyl]-4-(2,4-difluorophenyl)-2-methyl-5-((Z)-(5-[(methylamino)sulfonyl]-2- oxo-1,2-dihydro-3H-indol-3-ylidenemethyl)-1H-pyrrole-3-carboxamide was evaluated for its ability to bind the wild-type ABL kinase domain and the T315I ABL mutant in a titration experiment, as described above. The applied conditions were the same except for the saturating probe concentration (2, 3.3 and 0.2 μM for ABL wild-type unphosphorylated (0P), wild-type and T315I, respectively) and the probe final concentration (2, 3.3 and 0.2 μM for ABL wild-type unphosphorylated (0P), wild-type and T315I, respectively).

Also in this case, the results (Table 4) indicate that the probe could be fully displaced by ATPγS from all of the tested ABL constructs indicating that the indolinone binds in the ATP pocket. Imatinib, as expected, showed a higher affinity for the unphosphorylated rather than for the phosphorylated form of ABL, whereas no displacement was observed on the T315I ABL mutant.

TABLE 4

|  | Wild-type ABL 0P | Wild-type ABL | T315I ABL |
| --- | --- | --- | --- |
| Probe titration, KD (μM) | 0.2 ± 0.1 | 0.33 ± 0.12 | 0.02 ± 0.008 |
| ATPγS, KD' (μM) | 6.6 ± 1.6 (100% displ) | 4.8 ± 1 (100% displ) | 2.61 ± 0.9 (100% displ) |
| Imatinib, KD' (μM) | 0.021 ± 0.008 (100% displ) | 0.23 ± 0.09 (100% displ) | (0% displ) |

Taken together, these results show that the displacement assay is ATP site-dependent and the measured affinities are in line with published data on Imatinib (CARTER, T. A., et a)., ibid.; FABIAN, Miles A., et al., ibid.). ATP site-dependent displacement assay with recombinant ABL kinase domains.

Compound binding affinity with recombinant wild-type and T315I mutant ABL kinase domains was evaluated in the displacement assay as reported under 3.1 and testing the same pyrrolopyraxole compounds. Table 5 shows the affinity binding constant determination (KD) for different ABL constructs.

TABLE 5

|  | Wild-type ABL 0P KD (μM) | Wild-type ABL KD (μM) | T315I ABL KD (μM) |
| --- | --- | --- | --- |
| VX 680 (Vertex) | 0.058 ± 0.02 | 0.080 ± 0.01 | 0.043 ± 0.014 |
| Compound 1 | 0.278 ± 0.122 | 0.310 ± 0.026 | 0.037 ± 0.013 |
| Compound 2 | 0.107 ± 0.021 | 0.177 ± 0.032 | 0.015 ± 0.004 |
| Compound 3 | 0.350 ± 0.05 | 0.553 ± 0.136 | 0.070 ± 0.022 |
| Imatinib | 0.020 ± 0.006 | 0.122 ± 0.022 | 0% displ. |

Affinity binding constant (KD) toward T315I ABL mutant was also determined for additional exemplary compounds of the invention (Compounds 4 to 13 as defined above).

Results are reported below in Table 6.

TABLE 6

|  | T315I ABL mutant KD (μM) |
| --- | --- |
| Compound 4 | 0.0027 ± 0.001 |
| Compound 5 | 0.0053 ± 0.004 |
| Compound 6 | 0.0174 ± 0.006 |
| Compound 7 | 0.0168 ± 0.003 |
| Compound 8 | 0.0083 ± 0.0015 |
| Compound 9 | 0.0180 ± 0.0034 |
| Compound 10 | 0.0093 ± 0.0025 |
| Compound 11 | 0.0110 ± 0.0026 |
| Compound 12 | 0.0117 ± 0.0038 |
| Compound 13 | 0.0063 ± 0.0033 |
| Imatinib | 0% displ. |

The displacement assay was performed as described before, with 3 μM as the highest inhibitor concentration tested. Results showed in tables 5 and 6 are the average of three independent experiments. They indicate that all of the tested compounds were active on the T315I ABL mutant Example 4

Inhibition of ABL Activity in Cells

Materials and methods

Cloning of ABL Polypeptide

ABL cDNA (corresponding to residues 27-1130) was PCR amplified from a human testis cDNA library. Amplification was performed using the forward oligonucleotide:

(SEQ ID NO: 4)
5'GGGACAAGTTTGTACAAAAAAGCAGGCTTACTGGAAGTTCTGTTCCAG
GGGCCCGAAGCCCTTCAGCGGCCAGTAG-3'
and the reverse oligonucleotide:

(SEQ ID NO: 5)
5'GGGGACCACTTTGTACAAGAAAGCTGGGTTTTACCTCTGCACTATGTC
ACTG-3'

For cloning purposes, the oligonucleotides included attb sites in order to obtain an attb-flanked PCR product suitable for cloning using the Gateway® technology (Invitrogen). The resulting PCR product was cloned in the mammalian expression vector pcDNA3.1/nV5 DEST (Invitrogen). Cloning was performed accordingly to the protocols described in the Gateway® manual.

The Imatinib-resistant mutant T315I was generated by site-directed mutagenesis using the QuikChange® mutagenesis kit (Stratagene). Oligonucleotide used in the mutagenesis reaction was:

(SEQ ID NO: 6)
5'-CCCCGTTCTATATCATCATTGAGTTCATGACCTACG-3'.

Immunoblotting

Immunoblotting was performed according to standard methods. Cells were prepared in 125 mM Tris-HCl pH 6.8 and 2% SDS. Samples were sonicated and heated for 5 min at 95° C. 10 μg of protein extract, as determined by BCA™ Protein Assay (Pierce, Rockford, Ill.) was loaded on SDS-PAGE. Super signal chemiluminescence kit (Pierce, Rockford, Ill.) was used for detection. Immunoblot analysis was performed using the following antibodies: anti-ABL (SIGMA, catalogue no. A5844); anti-pY412-ABL (CELL SIGNALING, catalogue no. 2865); anti-Stat-5 (CELL SIGNALING, catalogue no. 9352); anti-pStat-5, anti-Crkl, anti p-Crkl, anti-EIF4e (BCR/ABL Activity Assay, CELL SIGNALING, catalogue no. 7130).

Results

Figure 2:
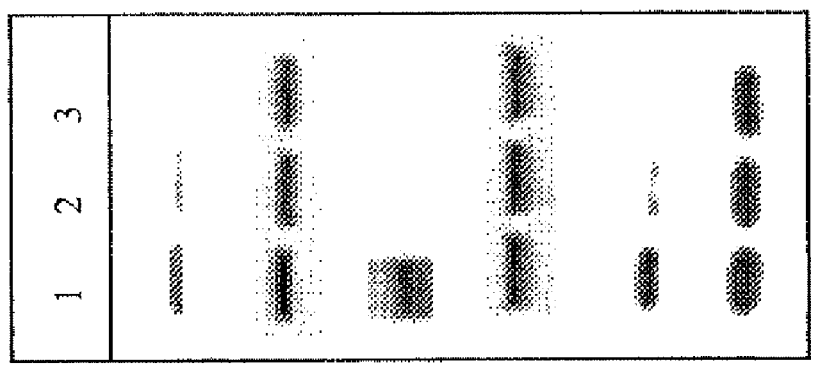
FIG. 2 is an immunoblotting showing the inhibition of BCR-ABL in K-562 leukemia cells treated with Compound 1 (lane 1) or Imatinib (lane 2). Inhibition of the BCR-ABL signaling was monitored analyzing the phosphorylation status of the downstream targets STAT5 or CRKL. Lane 1 shows untreated K-562 cells.

In order to confirm the inhibitory activity of one exemplary compound of the invention on endogenously expressing BCR-ABL cells, 3-(4-Piperidin-1-ylmethyl-benzoylamino)-1H-thieno[2,3-c]pyrazole-5-carboxylic acid (1-methyl-1-phenyl-ethyl)-amide (compound 1) was tested in K-562 leukemia cells, which bear the Philadelphia chromosome related to translocation of BCR-ABL. Cells were treated for one hour with compound I or Imatinib. Cells were collected and analyzed by immunoblotting for inhibition of ABL auto-phosphorylation of the tyrosine residue in position 412 (Y412), which is located in the kinase activation loop of ABL. Also known downstream signaling proteins such as Stat-5 or Crkl were analyzed for their phosphorylation status. Compound 1 and Imatinib (at a clinically relevant concentration), inhibit phosphorylation of Y412 and phosphorylation of the downstream mediators of BCR-ABL Stat-S and Crkl (FIG. 2)

confirming the expected mechanism of action, whereas no effect on Src was seen excluding a general effect on protein phosphorylation.

Figure 3:
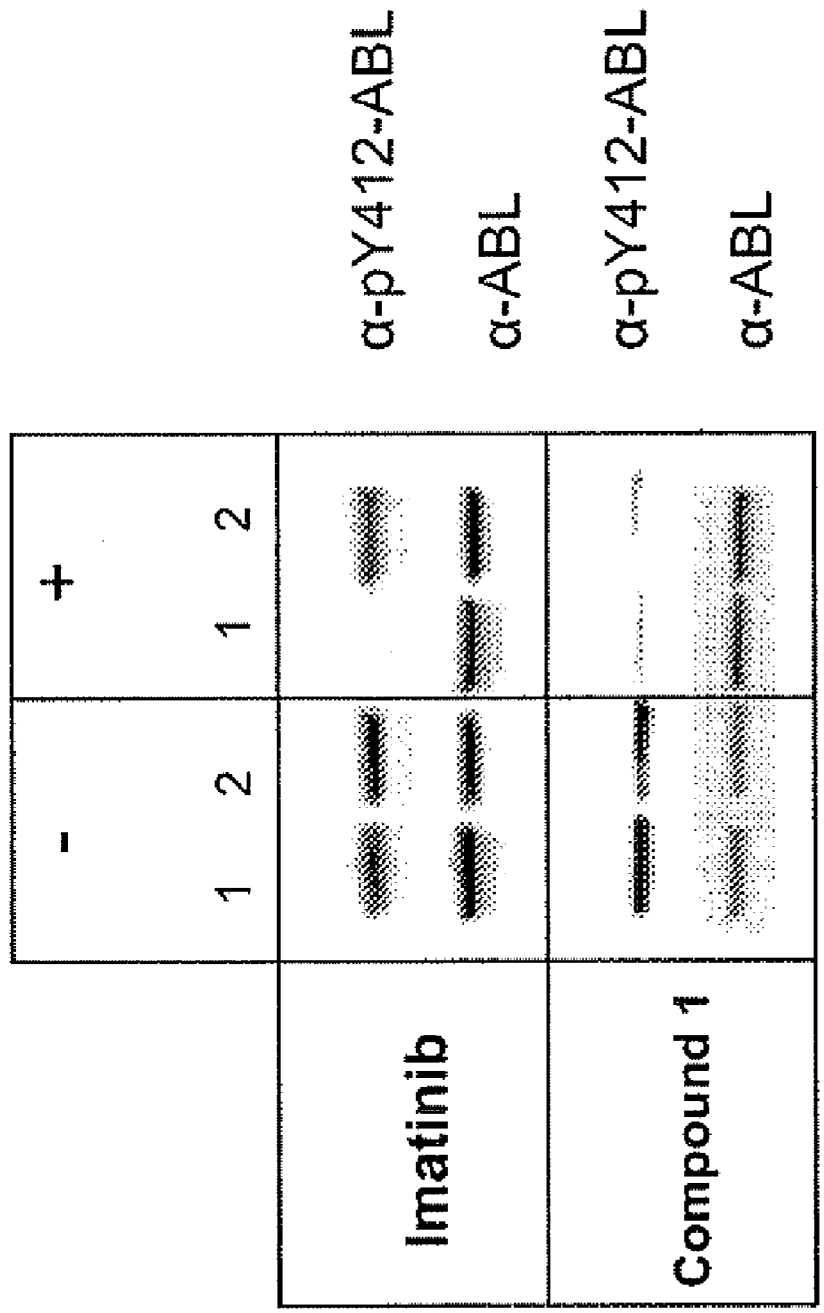
FIG. 3 is an immunoblotting showing the inhibition of wild-type and T315I mutant ABL by Compound 1 in HCT-116 transfected cells. HCT-116 colorectal tumor cells were transfected with an ABL wild-type (lane 1) or a T315I ABL mutant expression construct (lane 2). Cell lysates were analyzed by immunoblotting using antibodies against total ABL protein (α-ABL) or a phospho-specific antibody recognizing ABL when it is phosphorylated in position Y412 (α-pY412-ABL). A comparison between untreated (−) and treated (+) cells shows that compound 1 is capable of inhibiting both wild-type as well as T315I mutant ABL.

In order to test the cellular activity of Imatinib and compound 1 in cells on the T315I ABL mutant, HCT-116 cells were transfected with wild-type or mutant expression constructs and inhibitory activity was tested for Imatinib and compound 1 at 5 µM. As expected Imatinib showed inhibitory activity only on the wild-type ABL constructs, whereas the T315I ABL mutant construct was resistant. In contrast, compound 1 showed strong inhibitory activity for both wild-type and the T315I ABL mutant (FIG. 3).

The invention claimed is:

1. A method for inhibiting a BCR-ABL inhibitor-resistant tyrosine kinase activity comprising contacting a BCR-ABL inhibitor-resistant tyrosine kinase polypeptide with an effective amount of the compound of formula (I)

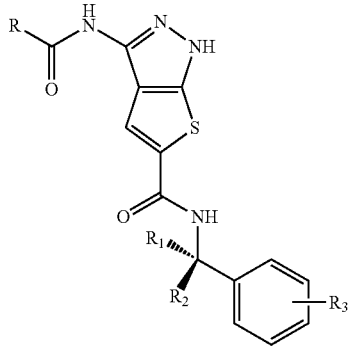

(I)

wherein R is an optionally substituted aryl or heteroaryl group;

$R_1$ and $R_2$ represent, the same or different and independently from each other, a hydrogen atom, a straight or branched $C_1$-$C_3$ alkyl or, taken together with the carbon atom to which they are bonded, $R_1$ and $R_2$ may form a $C_3$-$C_6$ cycloalkyl group; with the proviso that at least one of $R_1$ and $R_2$ is other than a hydrogen atom;

$R_3$ is a hydrogen or halogen atom or a group selected from hydroxy, cyano, straight or branched $C_1$-$C_3$ alkyl or $C_1$-$C_3$ alkoxy.

2. The method according to claim 1 wherein the BCR-ABL inhibitor-resistant tyrosine kinase polypeptide is a T315I mutant of ABL tyrosine kinase.

3. The method according to claim 2 wherein the BCR-ABL inhibitor is Imatinib.

4. A method of treating a BCR-ABL inhibitor-resistant T315I ABL-mediated disease, which comprises administering to a mammal in need thereof an effective amount of the compound of formula (I)

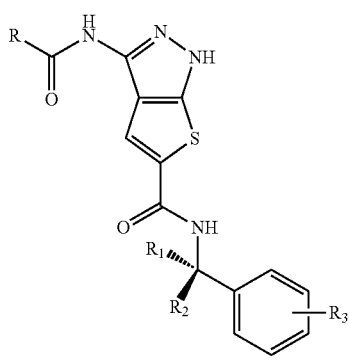

(I)

wherein R is an optionally substituted aryl or heteroaryl group;

$R_1$ and $R_2$ represent, the same or different and independently from each other, a hydrogen atom, a straight or branched $C_1$-$C_3$ alkyl or, taken together with the carbon atom to which they are bonded, $R_1$ and $R_2$ may form a $C_3$-$C_6$ cycloalkyl group; with the proviso that at least one of $R_1$ and $R_2$ is other than a hydrogen atom;

$R_3$ is a hydrogen or halogen atom or a group selected from hydroxy, cyano, straight or branched $C_1$-$C_3$ alkyl or $C_1$-$C_3$ alkoxy;

or a pharmaceutically acceptable salt thereof.

5. The method of claim 4 wherein said BCR-ABL inhibitor-resistant T315I ABL-mediated disease is BCR-ABL inhibitor-resistant leukemia.

6. The method of claim 5 wherein the disease is BCR-ABL inhibitor-resistant chronic myelogenous leukemia.

7. The method according to any one of claims 4 to 6 wherein the BCR-ABL inhibitor is Imatinib.

8. A method of treating BCR-ABL inhibitor-resistant T315I ABL-mediated disease, which comprises administering to a mammal in need thereof an effective amount of the compound of formula (II)

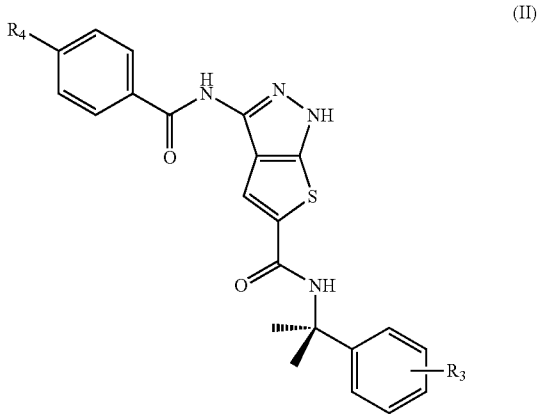

(II)

wherein $R_4$ is a group selected from azetidin-1-yl, pirrolidin-1-yl, piperidin-1-yl, (1-methyl-piperazin-4-yl), (morpholino-4-yl), (azetidin-1-yl)methyl, (pirrolidin-1-yl)methyl, (piperidin-1-yl)methyl, (1-methyl-piperazin-4-yl)methyl, (morpholino-4-yl)methyl, (1-methyl-piperidin-4-yloxy)methyl, (isopropyl amino)methyl; and $R_3$ is a hydrogen or fluorine or chlorine atom.

9. The method according to claim 1 wherein the compound is selected from the group consisting of:

N-(1-methyl-1-phenylethyl)-3-[(4-morpholin-4-ylbenzoyl)amino]-1H-thieno[2,3-c]pyrazole-5-carboxamide;

3-[(4-morpholin-4-ylbenzoyl)amino]-N-(1-phenylcyclopropyl)-1H-thieno[2,3-c]pyrazole-5-carboxamide;

N-(1-methyl-1-phenylethyl)-3-({4-[(1-methylpiperidin-4-yl)oxy]benzoyl}amino)-1H-thieno[2,3-c]-pyrazole-5-carboxamide;

3-({4-[(1-methylpiperidin-4-yl)oxy]benzoyl}amino)-N-(1-phenylcyclopropyl)-1H-thieno[2,3-c]pyrazole-5-carboxamide;

N-(1-methyl-1-phenylethyl)-3-({4-[(4-methylpiperazin-1-yl)methyl]benzoyl}amino)-1H-thieno[2,3-c]pyrazole-5-carboxamide;

N-(1-ethyl-1-phenylpropyl)-3-{[4-(4-methylpiperazin-1-yl)benzoyl]amino }-1H-thieno[2,3-c]pyrazole-5-carboxamide;

3-{[-4-(4-methylpiperazin-1-yl)benzoyl]amino}1-N-(1-phenylcyclopentyl)-1H-thieno-[2,3-c]pyrazole-5-carboxamide;

3-{[4-(4-methylpiperazin-1yl)benzoyl]amino)-N-(1-phenylcyclopropyl)-1H-thieno[2,3-c]pyrazole-5-carboxamide;

3-(4-Morpholin-4-yl-benzoylamino)-1H-thieno[2,3-c]pyrazole-5-carboxylic acid (1-ethyl-1-phenyl-propyl)-amide;

3-(4-Morpholin-4-yl-benzoylamino)-1H-thieno[2,3-c]pyrazole-5-carboxylic acid (1-phenyl-cyclopentyl)-amide;

3-[4-(4-Methyl-piperazin-1-yl)-benzoylamino]-1H-thieno[2,3-c]pyrazole-5-carboxylic acid [1-(3-chloro-phenyl)-1-methyl-ethyl]-amide;

3-(4-Morpholin-4-ylmethyl-benzoylamino)-1H-thieno[2,3-c]pyrazole-5-carboxylic acid (1-methyl-1-phenyl-ethyl)-amide;

3-(4-Piperidin-1-ylmethyl-benzoylamino)-1H-thieno[2,3-c]pyrazole-5-carboxylic acid (1-methyl-1-phenyl-ethyl)-amide;

3-[4-(Isopropylamino-methyl)-benzoylamino]-1H-thieno[2,3-c]pyrazole-5-carboxylic acid (1-methyl-1-phenyl-ethyl)-amide;

3-(4-Pyrrolidin-1-ylmethyl-benzoylamino)-1H-thieno[2,3-c]pyrazole-5-carboxylic acid (1-methyl-1-phenyl-ethyl)-amide;

3-[4-(4-Methyl-piperazin-1-yl)-benzoylamino]-1H-thieno[2,3-c]pyrazole-5-carboxylic acid [1-(4-fluoro-phenyl)-1-methyl-ethyl]-amide;

3-[4-(4-Methyl-piperazin-1-yl)-benzoylamino]-1H-thieno[2,3-c]pyrazole-5-carboxylic acid [1-(2-fluoro-phenyl)-1-methyl-ethyl]-amide;

3-[4-(4-Methyl-piperazin-1-yl)-benzoylamino]-1H-thieno[2,3-c]pyrazole-5-carboxylic acid [1-(3-fluoro-phenyl)-1-methyl-ethyl]-amide;

3-(4-Morpholin-4-ylmethyl-benzoylamino)-1H-thieno[2,3-c]pyrazole-5-carboxylic acid [1-(3-fluoro-phenyl)-1-methyl-ethyl]-amide;

3-(4-Pyrrolidin-1-ylmethyl-benzoylamino)-1H-thieno[2,3-c]pyrazole-5-carboxylic acid [1-(3-fluoro-phenyl)-1-methyl-ethyl]-amide;

3-(4-Piperidin-1-ylmethyl-benzoylamino)-1H-thieno[2,3-c]pyrazole-5-carboxylic acid [1-(2-fluoro-phenyl)-1-methyl-ethyl]-amide;

3-(4-Azetidin-1-ylmethyl-benzoylamino)-1H-thieno[2,3-c]pyrazole-5-carboxylic acid (1-methyl-1-phenyl-ethyl)-amide;

3-(4-Morpholin-4-yl-benzoylamino)-1H-thieno[2,3-c]pyrazole-5-carboxylic acid [1-(2-fluoro-phenyl)-1-methyl-ethyl]-amide;

3-(4-Morpholin-4-yl-benzoylamino)-1H-thieno[2,3-c]pyrazole-5-carboxylic acid [1-(3-fluoro-phenyl)-1-methyl-ethyl]-amide;

3-(4-Morpholin-4-yl-benzoylamino)-1H-thieno[2,3-c]pyrazole-5-carboxylic acid [1-(4-fluoro-phenyl)-1-methyl-ethyl]-amide;

3-(4-Piperidin-1-ylmethyl-benzoylamino)-1H-thieno[2,3-c]pyrazole-5-carboxylic acid [1-(4-fluoro-phenyl)-1-methyl-ethyl]-amide;

3-(4-Morpholin-4-ylmethyl-benzoylamino)-1H-thieno[2,3-c]pyrazole-5-carboxylic acid [1-(2-fluoro-phenyl)-1-methyl-ethyl]-amide;

3-(4-Morpholin-4-ylmethyl-benzoylamino)-1H-thieno[2,3-c]pyrazole-5-carboxylic acid [i-(4-fluoro-phenyl)-1-methyl-ethyl]-amide;

3-(4-Piperidin-1-ylmethyl-benzoylamino)-1H-thieno[2,3-c]pyrazole-5-carboxylic acid [1-(3-fluoro-phenyl)-1-methyl-ethyl]-amide3-(4-Azetidin-1-ylmethyl-benzoylamino)-1H-thieno2,3-c]pyrazole-5-carboxylic acid [1-(2-fluoro-phenyl)-1-methyl-ethyl]-amide;

3-(4-Dimethylaminomethyl-benzoylamino)-1H-thieno[2,3-c]pyrazole-5-carboxylic acid (1-methyl-1-phenyl-ethyl)-amide;

3-(4-Cyclopropylaminomethyl-benzoylamino)-1H-thieno[2,3-c]pyrazole-5-carboxylic acid (1-methyl-1-phenyl-ethyl)-amide;

3-(4-Cyclobutylaminomethyl-benzoylamino)-1H-thieno[2,3-c]pyrazole-5-carboxylic acid (1-methyl-1-phenyl-ethyl)-amide;

3-{4-[(Isopropyl-methyl-amino)-methyl]-benzoylamino}-1H-thieno[2,3-c]pyrazole-5-carboxylic acid (1-methyl-1-phenyl-ethyl)-amide;

3-(4-Cyclopentylaminomethyl-benzoylamino)-1H-thieno[2,3-c]pyrazole-5-carboxylic acid (1-methyl-1-phenyl-ethyl)-amide;

3-4-[(Diisopropylamino)-methyl]benzoylamino)-1H-thieno[2,3-c]pyrazole-5-carboxylic acid (1-methyl-1-phenyl-ethyl)-amide;

3-(4-Pyrrolidin-1-ylmethyl-benzoylamino)-1H-thieno[2,3-c]pyrazole-5-carboxylic acid [1-(2-fluoro-phenyl)-1-methyl-ethyl)-amide;

3-[4-(4-Methyl-piperazin-1-yl)-benzoylamino]-1H-thieno[2,3-c]pyrazole-5-carboxylic acid [1-methyl-1-(2-fluoro-phenyl)-ethyl]amide;

3-({4-[(1-methylpiperidin-4-yl-)oxy]benzoyl}amino)-1H-thieno[2,3-c]pyrazole-5-carboxylic acid [1-methyl-1-(2-fluoro-phenyl)-ethyl]-amide;

3-(4-Cyclopropylaminomethyl-benzoylamino)-1H-thieno[2,3-c]pyrazole-5-carboxylic acid 1-(2-fluoro-phenyl)-1-methyl-ethyl]-amide;

3-[4-(Isopropylamino-methyl)-benzoylamino]-1H-thieno[2,3-c]pyrazole-5-carboxylic acid 1-(2-fluoro-phenyl)-1-methyl-ethyl]-amide;

3-Benzoylamino-1H-thieno[2,3-c]-pyrazole-5-carboxylic acid (1-methyl-1-phenyl-ethyl)-amide;

3-(4-Azepan-1-ylmethyl-benzoylamino)-1H-thieno[2,3-c]pyrazole-5-carboxylic acid (1-methyl-1-phenyl-ethyl)-amide;

3-(4-Azepan-1-ylmethyl-benzoylamino)-1H-thieno[2,3-c]pyrazole-5-carboxylic acid [1-(2-fluoro-phenyl)-1-methyl-ethyl]-amide.

10. The method of claim 9 wherein the compound is selected from the group consisting of:

N-(1-methyl-1-phenylethyl)-3-({4-[(1-methylpiperidin-4-yl)oxy]benzoyl}-amino)-1H-thieno[2,3-c]pyrazole-5-carboxamide;

3-(4-Piperidin-1-ylmethyl-benzoylamino)-1H-thieno[2,3-c]pyrazole-5-carboxylic acid (1-methyl-1-phenyl-ethyl)-amide;

N-(-methyl-1-phenylethyl)-3-{[4-(4-methylpiperazin-1-yl)benzoyl}amino)-1H-thieno [2,3-c]pyrazole-5-carboxamide;

N-(1-methyl-1-phenylethyl)-3-({4-[(4-methylpiperazin-1-yl)methyl]benzoyl}amino)-1H-thieno[2,3-c]pyrazole-5-carboxamide;

3-(4-Piperidin-1-ylmethyl-benzoylamino)-1H-thieno[2,3-c]pyrazole-5-carboxylic acid [1-(2-fluoro-phenyl)-1-methyl-ethyl]-amide.

11. The method according to claim 10 wherein the compound is 3-(4-Piperidin-1-ylmethyl-benzoylamino)-1H-thieno[2,3-c]pyrazole-5-carboxylic acid (1-methyl-1-phenyl-ethyl)-amide.

12. A screening method for the identification of compounds capable of binding the ATP pocket of a kinase protein, comprising the steps of:
providing a reaction mixture comprising the kinase protein, an indolinone having affinity for the ATP pocket of the said kinase protein and capable of generating a fluorescent signal upon binding to the said ATP pocket, and serial dilutions of the test compound, comparing the fluorescent signal generated in the absence of the test compound with the fluorescent signal generated in the presence of different concentrations of the test compound, whereby a decreased level of fluorescence indicates the ability of the test compound to displace the indolinone.

13. The method of claim 12 wherein the kinase protein and the indolinone are pre-mixed.

14. The method of claim 12 wherein the kinase protein and the test compound are pre-mixed.

15. The method according to any one of claims 12 to 14 wherein the kinase protein is an ABL kinase.

16. The method of claim 15 wherein the ABL kinase is T315I mutant ABL kinase.

17. The method according to claim 12 wherein the indolinone is a compound of formula (III)

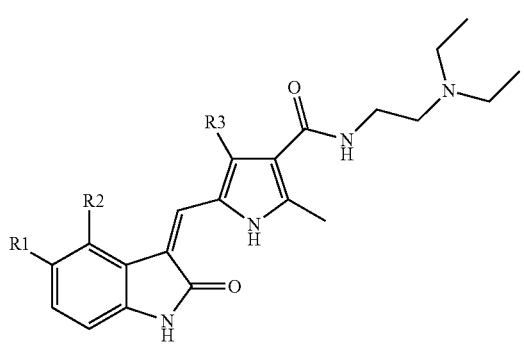

(III)

wherein R1 is hydrogen or methylamino-sulfonyl or benzyl-sulfonyl, R2 is hydrogen or methyl, R3 is methyl or 4-chlorophenyl or 2,4-difluorophenyl.

18. The method according to claim 17 wherein the indolinone is selected from the group consisting of:
2,4-dimethyl-5-[2-oxo-5-phenylmethanesulfonyl-1,2-dihydro-indol-(3Z)-ylidenemethyl]-1H-pyrrole-3-carboxylic acid (2-diethylamino-ethyl)-amide;
4-(4-chlorophenyl)-N-[2-(diethylamino)ethyl]-2-methyl-5-((Z)-{5-[(methylamino)sulfonyl]-2-oxo-1,2-dihydro-3H-indol-3-ylidene}methyl)-1H-pyrrole-3-carboxamide;
N-[2-(diethylamino)ethyl]-4-(2,4-difluorophenyl)-2-methyl-5-((Z)-{5-[(methylamino)sulfonyl]-2-oxo-1,2-dihydro-3H-indol-3-ylidene}methyl)-1H-pyrrole-3-carboxamide;
4-(4-chlorophenyl)-N-[2-(diethylamino)ethyl]-2-methyl-5-[(Z)-(4-methyl-2-oxo-1,2-dihydro-3H-indol-3-ylidene)methyl]-1H-pyrrole-3-carboxamide.

19. A method for inhibiting a BCR-ABL inhibitor-resistant tyrosine kinase activity comprising contacting a BCR-ABL inhibitor-resistant tyrosine kinase polypeptide with an effective amount of the compound of formula (II)

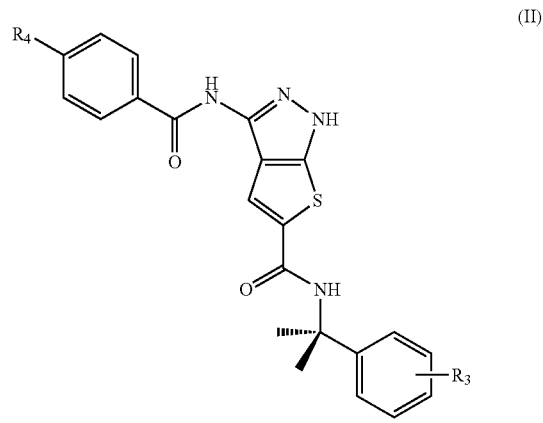

(II)

wherein R4 is a group selected from azetidin-1-yl, pirrolidin-1-yl, piperidin-1-yl, (1-methyl-piperazin-4-yl), (morpholino-4-yl), (azetidin-1-yl)methyl, (pirrolidin-1-yl)methyl, (piperidin-1-yl)methyl, (1-methyl-piperazin-4-yl)methyl, (morpholino-4-yl)methyl, (1-methyl-piperidin-4-yloxy)methyl, (isopropyl amino)methyl; and
R3 is a hydrogen or fluorine or chlorine atom.

20. The method according to claim 4 wherein the compound is selected from the group consisting of:
N-(1-methyl-1-phenylethyl)-3-[(4-morpholin-4-ylbenzoyl)amino]-1H-thieno[2,3-c]pyrazole-5-carboxamide;
3-[(4-morpholin-4-ylbenzoyl)amino]-N-(1-phenylcyclopropyl)-1H-thieno[2,3-c]pyrazole-5-carboxamide;
N-(1-methyl-1-phenylethyl)-3-({4-[(1-methylpiperidin-4-yl)oxy]benzoyl}amino)-1H-thieno[2,3-c]-pyrazole-5-carboxamide;
3-({4-[(1-methylpiperidin-4-yl)oxy]benzoyl}amino)-N-(1-phenylcyclopropyl)-1H-thieno[2,3-c]pyrazole-5-carboxamide;
N-(1-methyl-1-phenylethyl)-3-({4-[(4-methylpiperazin-1-yl)methyl]benzoyl}amino)-1H-thieno[2,3-c]pyrazole-5-carboxamide;
N-(1-ethyl-1-phenylpropyl)-3-{[4-(4-methylpiperazin-1-yl)benzoyl]amino}-1H-thieno [2,3-c]pyrazole-5-carboxamide;
3-{[-4-(4-methylpiperazin-1-yl)benzoyl]amino}-N-(1-phenylcyclopentyl)- 1H-thieno-[2,3-c]pyrazole-5-carboxamide;
3-{[4-(4-methylpiperazin-1-yl)benzoyl]amino}-N-(1-phenylcyclopropyl)-1H-thieno[2,3-c]pyrazole-5-carboxamide;
3-(4-Morpholin-4-yl-benzoylamino)-1H-thieno[2,3-c]pyrazole-5-carboxylic acid (1-ethyl-1-phenyl-propyl)-amide;

3-(4-Morpholin-4-yl-benzoylamino)-1H-thieno[2,3-c] pyrazole-5-carboxylic acid (1-phenyl-cyclopentyl)-amide;

3-[4-(4-Methyl-piperazin-1-yl)-benzoylamino]-1H-thieno[2,3-c]pyrazole-5-carboxylic acid [1-(3-chloro-phenyl)-1-methyl-ethyl]-amide;

3-(4-Morpholin-4-ylmethyl-benzoylamino)-1H-thieno[2,3-c]pyrazole-5-carboxylic acid (1-methyl-1-phenyl-ethyl)-amide;

3-(4-Piperidin-1-ylmethyl-benzoylamino)-1H-thieno[2,3-c]pyrazole-5-carboxylic acid (1-methyl-1-phenyl-ethyl)-amide;

3-[4-(Isopropylamino-methyl)-benzoylamino]-1H-thieno[2,3-c]pyrazole-5-carboxylic acid (1-methyl-1-phenyl-ethyl)-amide;

3-(4-Pyrrolidin-1-ylmethyl-benzoylamino)-1H-thieno[2,3-c]pyrazole-5-carboxylic acid (1-methyl-1-phenyl-ethyl)-amide;

3-[4-(4-Methyl-piperazin-1-yl)-benzoylamino]-1H-thieno[2,3-c]pyrazole-5-carboxylic acid [1-(4-fluoro-phenyl)-1-methyl-ethyl]-amide;

3-[4-(4-Methyl-piperazin-1-yl)-benzoylamino]-1H-thieno[2,3-c]pyrazole-5-carboxylic acid [1-(2-fluoro-phenyl)-1-methyl-ethyl]-amide;

3-[4-(4-Methyl-piperazin-1-yl)-benzoylamino]-1H-thieno[2,3-c]pyrazole-5-carboxylic acid [1-(3-fluoro-phenyl)-1-methyl-ethyl]-amide;

3-(4-Morpholin-4-ylmethyl-benzoylamino)-1H-thieno[2,3-c]pyrazole-5-carboxylic acid [1-(3-fluoro-phenyl)-1-methyl-ethyl]-amide;

3-(4-Pyrrolidin-1-ylmethyl-benzoylamino)-1H-thieno[2,3-c]pyrazole-5-carboxylic acid [1-(3-fluoro-phenyl)-1-methyl-ethyl]-amide;

3-(4-Piperidin-1-ylmethyl-benzoylamino)-1H-thieno[2,3-c]pyrazole-5-carboxylic acid [1-(2-fluoro-phenyl)-1-methyl-ethyl]-amide;

3-(4-Azetidin-1-ylmethyl-benzoylamino)-1H-thieno[2,3-c]pyrazole-5-carboxylic acid (1-methyl-1-phenyl-ethyl)-amide;

3-(4-Morpholin-4-yl-benzoylamino)-1H-thieno[2,3-c] pyrazole-5-carboxylic acid [1-(2-fluoro-phenyl)-1-methyl-ethyl]-amide;

3-(4-Morpholin-4-yl-benzoylamino)-1H-thieno[2,3-c] pyrazole-5-carboxylic acid [1-(3-fluoro-phenyl)-1-methyl-ethyl]-amide;

3-(4-Morpholin-4-yl-benzoylamino)-1H-thieno[2,3-c] pyrazole-5-carboxylic acid [1-(4-fluoro-phenyl)-1-methyl-ethyl]-amide;

3-(4-Piperidin-1-ylmethyl-benzoylamino)-1H-thieno[2,3-c]pyrazole-5-carboxylic acid [1-(4-fluoro-phenyl)-1-methyl-ethyl]-amide;

3-(4-Morpholin-4-ylmethyl-benzoylamino)-1H-thieno[2,3-c]pyrazole-5-carboxylic acid [1-(2-fluoro-phenyl)-1-methyl-ethyl]-amide;

3-(4-Morpholin-4-ylmethyl-benzoylamino)-1H-thieno[2,3-c]pyrazole-5-carboxylic acid [i-(4-fluoro-phenyl)-1-methyl-ethyl]-amide;

3-(4-Piperidin-1-ylmethyl-benzoylamino)-1H-thieno[2,3-c]pyrazole-5-carboxylic acid [1-(3-fluoro-phenyl)-1-methyl-ethyl]-amide3-(4-Azetidin-1-ylmethyl-benzoylamino)-1H-thieno2,3-c]pyrazole-5-carboxylic acid [1-(2-fluoro-phenyl)-1-methyl-ethyl]-amide;

3-(4-Dimethylaminomethyl-benzoylamino)-1H-thieno[2,3-c]pyrazole-5-carboxylic acid (1-methyl-1-phenyl-ethyl)-amide;

3-(4-Cyclopropylaminomethyl-benzoylamino)-1H-thieno[2,3-c]pyrazole-5-carboxylic acid (1-methyl-1-phenyl-ethyl)-amide;

3-(4-Cyclobutylaminomethyl-benzoylamino)-1H-thieno[2,3-c]pyrazole-5-carboxylic acid (1-methyl-1-phenyl-ethyl)-amide;

3-{4-[(Isopropyl-methyl-amino)-methyl]-benzoylamino}-1H-thieno[2,3-c]pyrazole-5-carboxylic acid (1-methyl-1-phenyl-ethyl)-amide;

3-(4-Cyclopentylaminomethyl-benzoylamino)-1H-thieno[2,3-c]pyrazole-5-carboxylic acid (1-methyl-1-phenyl-ethyl)-amide;

3-4- [(Diisopropylamino)-methyl]-benzoylamino)-1H-thieno[2,3-c]pyrazole-5-carboxylic acid (1-methyl-1-phenyl-ethyl)-amide;

3-(4-Pyrrolidin-1-ylmethyl-benzoylamino)-1H-thieno[2,3-c]pyrazole-5-carboxylic acid [1-(2-fluoro-phenyl)-1-methyl-ethyl]-amide;

3-[4-(4-Methyl-piperazin-1-yl)-benzoylamino]-1H-thieno[2,3-c]pyrazole-5-carboxylic acid [1-methyl-1-(2-fluoro-phenyl)-ethyl]-amide;

3-({4-[(1-methylpiperidin-4-yl)oxy]benzoyl}amino)-1H-thieno[2,3-c]pyrazole-5-carboxylic acid [1-methyl-1-(2-fluoro-phenyl)-ethyl]-amide;

3-(4-Cyclopropylaminomethyl-benzoylamino)-1H-thieno[2,3-c]pyrazole-5-carboxylic acid 1-(2-fluoro-phenyl)-1-methyl-ethyl]-amide;

3-[4-(Isopropylamino-methyl)-benzoylamino]-1H-thieno[2,3-c]pyrazole-5-carboxylic acid 1-(2-fluoro-phenyl)-1-methyl-ethyl]-amide;

3-Benzoylamino-1H-thieno[2,3-c]-pyrazole-5-carboxylic acid (1-methyl-1-phenyl-ethyl)-amide;

3-(4-Azepan-1-ylmethyl-benzoylamino)-1H-thieno[2,3-c]pyrazole-5-carboxylic acid (1-methyl-1-phenyl-ethyl)-amide;

3-(4-Azepan-1-ylmethyl-benzoylamino)-1H-thieno[2,3-c]pyrazole-5-carboxylic acid [1-(2-fluoro-phenyl)-1-methyl-ethyl]-amide.

21. The method according to claim 20 wherein the compound is selected from the group consisting of:

N-(1-methyl-1-phenylethyl)-3-({4-[(1-methylpiperidin-4-yl)oxy]benzoyl}-amino)-1H-thieno[2,3-c]pyrazole-5-carboxamide;

3-(4-Piperidin-1-ylmethyl-benzoylamino)-1H-thieno[2,3-c]pyrazole-5-carboxylic acid (1-methyl-1-phenyl-ethyl)-amide;

N-(-methyl-1-phenylethyl)-3-{[4-(4-methylpiperazin-1-benzoyl}amino)-1H -thieno[2,3-c]pyrazole-5-carboxamide;

N-(1-methyl-1-phenylethyl)-3-({4-[(4-methylpiperazin-1-methyl]benzoyl}amino)-1H-thieno[2,3-c]pyrazole-5-carboxamide;

3-(4-Piperidin-1-ylmethyl-benzoylamino)-1H-thieno[2,3-c]pyrazole-5-carboxylic acid [1-(2-fluoro-phenyl)-1-methyl-ethyl]-amide.

22. The method according to claim 21 wherein the compound is 3-(4-Piperidin-1-ylmethyl-benzoylamino)-1H-thieno[2,3-c]pyrazole-5-carboxylic acid (1-methyl-1-phenyl-ethyl)-amide.

23. The method according to claim 8 wherein the compound is selected from the group consisting of:

N-(1-methyl-1-phenylethyl)-3-[(4-morpholin-4-ylbenzoyl)amino]-1H-thieno[2,3-c]pyrazole-5-carboxamide;

3-[(4-morpholin-4-ylbenzoyl)amino]-N-(1-phenylcyclopropyl)-1H-thieno[2,3-c]pyrazole-5-carboxamide;

N-(1-methyl-1-phenylethyl)-3-({4-[(1-methylpiperidin-4-yl)oxy]benzoyl}amino)-1H-thieno[2,3-c]-pyrazole-5-carboxamide;

3-({4-[(1-methylpiperidin-4-yl)oxy]benzoyl}amino)-N-(1-phenylcyclopropyl)-1H-thieno[2,3-c]pyrazole-5-carboxamide;

N-(1-methyl-1-phenylethyl)-3-({4-[(4-methylpiperazin-1-yl)methyl]benzoyl}amino)-1H-thieno[2,3-c]pyrazole-5-carboxamide;

N-(1-ethyl-1-phenylpropyl)-3-{[4-(4-methylpiperazin-1-yl)benzoyl]amino}-1H-thieno[2,3-c]pyrazole-5-carboxamide;

3- {[-4-(4-methylpiperazin-1-yl)benzoyl]amino}-N-(1-phenylcyclopentyl)-1H-thieno-[2,3-c]pyrazole-5-carboxamide;

3- {[4-(4-methylpiperazin-1-yl)benzoyl]amino)-N-(1-phenylcyclopropyl)-1H-thieno[2,3-c]pyrazole-5-carboxamide;

3-(4-Morpholin-4-yl-benzoylamino)-1H-thieno[2,3-c]pyrazole-5-carboxylic acid (1-ethyl-1-phenyl-propyl)-amide;

3-(4-Morpholin-4-yl-benzoylamino)-1H-thieno[2,3-c]pyrazole-5-carboxylic acid (1-phenyl-cyclopentyl)-amide;

3-[4-(4-Methyl-piperazin-1-yl)-benzoylamino]-1H-thieno[2,3-c]pyrazole-5-carboxylic acid [1-(3-chloro-phenyl)-1-methyl-ethyl]-amide;

3-(4-Morpholin-4-ylmethyl-benzoylamino)-1H-thieno[2,3-c]pyrazole-5-carboxylic acid (1-methyl-1-phenyl-ethyl)-amide;

3-(4-Piperidin-1-ylmethyl-benzoylamino)-1H-thieno[2,3-c]pyrazole-5-carboxylic acid (1-methyl-1-phenyl-ethyl)-amide;

3-[4-(Isopropylamino-methyl)-benzoylamino]-1H-thieno[2,3-c]pyrazole-5-carboxylic acid (1-methyl-1-phenyl-ethyl)-amide;

3-(4-Pyrrolidin-1-ylmethyl-benzoylamino)-1H-thieno[2,3-c]pyrazole-5-carboxylic acid (1-methyl-1-phenyl-ethyl)-amide;

3-[4-(4-Methyl-piperazin-1-yl)-benzoylamino]-1H-thieno[2,3-c]pyrazole-5-carboxylic acid [1-(4-fluoro-phenyl)-1-methyl-ethyl]-amide;

3-[4-(4-Methyl-piperazin-1-yl)-benzoylamino]-1H-thieno[2,3-c]pyrazole-5-carboxylic acid [1-(2-fluoro-phenyl)-1-methyl-ethyl]-amide;

3-[4-(4-Methyl-piperazin-1-yl)-benzoylamino]-1H-thieno[2,3-c]pyrazole-5-carboxylic acid [1-(3-fluoro-phenyl)-1-methyl-ethyl]-amide;

3-(4-Morpholin-4-ylmethyl-benzoylamino)-1H-thieno[2,3-c]pyrazole-5-carboxylic acid [1-(3-fluoro-phenyl)-1-methyl-ethyl]-amide;

3-(4-Pyrrolidin-1-ylmethyl-benzoylamino)-1H-thieno[2,3-c]pyrazole-5-carboxylic acid [1-(3-fluoro-phenyl)-1-methyl-ethyl]-amide;

3-(4-Piperidin-1-ylmethyl-benzoylamino)-1H-thieno[2,3-c]pyrazole-5-carboxylic acid [1-(2-fluoro-phenyl)-1-methyl-ethyl]-amide;

3-(4-Azetidin-1-ylmethyl-benzoylamino)-1H-thieno[2,3-c]pyrazole-5-carboxylic acid (1-methyl-1-phenyl-ethyl)-amide;

3-(4-Morpholin-4-yl-benzoylamino)-1H-thieno[2,3-c]pyrazole-5-carboxylic acid [1-(2-fluoro-phenyl)-1-methyl-ethyl]-amide;

3-(4-Morpholin-4-yl-benzoylamino)-1H-thieno[2,3-c]pyrazole-5-carboxylic acid [1-(3-fluoro-phenyl)-1-methyl-ethyl]-amide;

3-(4-Morpholin-4-yl-benzoylamino)-1H-thieno[2,3-c]pyrazole-5-carboxylic acid [1-(4-fluoro-phenyl)-1-methyl-ethyl]-amide;

3-(4-Piperidin-1-ylmethyl-benzoylamino)-1H-thieno[2,3-c]pyrazole-5-carboxylic acid [1-(4-fluoro-phenyl)-1-methyl-ethyl]-amide;

3-(4-Morpholin-4-ylmethyl-benzoylamino)-1H-thieno[2,3-c]pyrazole-5-carboxylic acid [1-(2-fluoro-phenyl)-1-methyl-ethyl]-amide;

3-(4-Morpholin-4-ylmethyl-benzoylamino)-1H-thieno[2,3-c]pyrazole-5-carboxylic acid [i-(4-fluoro-phenyl)-1-methyl-ethyl]-amide;

3-(4-Piperidin-1-ylmethyl-benzoylamino)-1H-thieno[2,3-c]pyrazole-5-carboxylic acid [1-(3-fluoro-phenyl)-1-methyl-ethyl]-amide3-(4-Azetidin-1-ylmethyl-benzoylamino)-1H-thieno2,3-c]pyrazole-5-carboxylic acid [1-(2-fluoro-phenyl)-1-methyl-ethyl]-amide;

3-(4-Dimethylaminomethyl-benzoylamino)-1H-thieno[2,3-c]pyrazole-5-carboxylic acid (1-methyl-1-phenyl-ethyl)-amide;

3-(4-Cyclopropylaminomethyl-benzoylamino)-1H-thieno[2,3-c]pyrazole-5-carboxylic acid (1-methyl-1-phenyl-ethyl)-amide;

3-(4-Cyclobutylaminomethyl-benzoylamino)-1H-thieno[2,3-c]pyrazole-5-carboxylic acid (1-methyl-1-phenyl-ethyl)-amide;

3-{4-[(Isopropyl-methyl-amino)-methyl]-benzoylamino}-1H-thieno[2,3-c]pyrazole-5-carboxylic acid (1-methyl-1-phenyl-ethyl)-amide;

3-(4-Cyclopentylaminomethyl-benzoylamino)-1H-thieno[2,3-c]pyrazole-5-carboxylic acid (1-methyl-1-phenyl-ethyl)-amide;

3-4-[(Diisopropylamino)-methyl]benzoylamino)-1H-thieno[2,3-c]pyrazole-5-carboxylic acid (1-methyl-1-phenyl-ethyl)-amide;

3-(4-Pyrrolidin-1-ylmethyl-benzoylamino)-1H-thieno[2,3-c]pyrazole-5-carboxylic acid [1-(2-fluoro-phenyl)-1-methyl-ethyl]-amide;

3-[4-(4-Methyl-piperazin-1-yl)-benzoylamino]-1H-thieno[2,3-c]pyrazole-5-carboxylic acid [1-methyl-1-(2-fluoro-phenyl)-ethyl]-amide;

3-({4-[(1-methylpiperidin-4-yl-)oxy]benzoyl}amino)-1H-thieno[2,3-c]pyrazole-5-carboxylic acid [1-methyl-1-(2-fluoro-phenyl)-ethyl]-amide;

3-(4-Cyclopropylaminomethyl-benzoylamino)-1H-thieno[2,3-c]pyrazole-5-carboxylic acid 1-(2-fluoro-phenyl)-1-methyl-ethyl]-amide;

3-[4-(Isopropylamino-methyl)-benzoylamino]-1H-thieno[2,3-c]pyrazole-5-carboxylic acid 1-(2-fluoro-phenyl)-1-methyl-ethyl]-amide;

3-Benzoylamino-1H-thieno[2,3-c]-pyrazole-5-carboxylic acid (1-methyl-1-phenyl-ethyl)-amide;

3-(4-Azepan-1-ylmethyl-benzoylamino)-1H-thieno[2,3-c]pyrazole-5-carboxylic acid (1-methyl-1-phenyl-ethyl)-amide;

3-(4-Azepan-1-ylmethyl-benzoylamino)-1H-thieno[2,3-c]pyrazole-5-carboxylic acid [1-(2-fluoro-phenyl)-1-methyl-ethyl]-amide.

24. The method according to claim 23 wherein the compound is selected from the group consisting of:

N-(1-methyl-1-phenylethyl)-3-({4-[(1-methylpiperidin-4-yl)oxy]benzoyl}- amino)-1H-thieno[2,3-c]pyrazole-5-carboxamide;

3-(4-Piperidin-1-ylmethyl-benzoylamino)-1H-thieno[2,3-c]pyrazole-5-carboxylic acid (1-methyl-1-phenyl-ethyl)-amide;

N-(-methyl-1-phenylethyl)-3-{[4-(4-methylpiperazin-1-yl)benzoyl]amino)-1H-thieno[2,3-c]pyrazole-5-carboxamide;

N-(1-methyl-1-phenylethyl)-3-({4-[(4-methylpiperazin-1-yl)methyl]benzoyl}amino)-1H-thieno[2,3-c]pyrazole-5-carboxamide;

3-(4-Piperidin-1-ylmethyl-benzoylamino)-1H-thieno[2,3-c]pyrazole-5-carboxylic acid [1-(2-fluoro-phenyl)-1-methyl-ethyl]-amide.

25. The method according to claim 24 wherein the compound is 3-(4-Piperidin-1-ylmethyl-benzoylamino)-1H-thieno[2,3-c]pyrazole-5-carboxylic acid (1-methyl-1-phenyl-ethyl)-amide.

* * * * *

SEQUENCE LISTING

<160> NUMBER OF SEQ ID NOS: 6

<210> SEQ ID NO 1
<211> LENGTH: 75
<212> TYPE: DNA
<213> ORGANISM: Artificial Sequence
<220> FEATURE:
<223> OTHER INFORMATION: forward oliognucleotide

<400> SEQUENCE: 1
ggggacaagt ttgtacaaaa aagcaggctt actggaagtt ctgttccagg ggccctcccc    60
caactacgac aagtg                                                     75

<210> SEQ ID NO 2
<211> LENGTH: 54
<212> TYPE: DNA
<213> ORGANISM: Artificial Sequence
<220> FEATURE:
<223> OTHER INFORMATION: reverse oligonucleotide

<400> SEQUENCE: 2
ggggaccact ttgtacaaga aagctgggtt ttatttcccc agctcctttt ccac          54

<210> SEQ ID NO 3
<211> LENGTH: 36
<212> TYPE: DNA
<213> ORGANISM: Artificial Sequence
<220> FEATURE:
<223> OTHER INFORMATION: mutagenesis oligonucleotide

<400> SEQUENCE: 3
ccccgttcta tatcatcatt gagttcatga cctacg                              36

<210> SEQ ID NO 4
<211> LENGTH: 77
<212> TYPE: DNA
<213> ORGANISM: Artificial Sequence
<220> FEATURE:
<223> OTHER INFORMATION: forward oligonucleotide

<400> SEQUENCE: 4
ggggacaagt ttgtacaaaa aagcaggctt actggaagtt ctgttccagg ggcccgaagc    60
ccttcagcgg ccagtag                                                   77

<210> SEQ ID NO 5
<211> LENGTH: 52
<212> TYPE: DNA
<213> ORGANISM: Artificial Sequence
<220> FEATURE:
<223> OTHER INFORMATION: reverse oligonucleotide

<400> SEQUENCE: 5
ggggaccact ttgtacaaga aagctgggtt ttacctctgc actatgtcac tg            52

<210> SEQ ID NO 6
<211> LENGTH: 36

```
<212> TYPE: DNA
<213> ORGANISM: Artificial Sequence
<220> FEATURE:
<223> OTHER INFORMATION: mutagenesis oligonucleotide

<400> SEQUENCE: 6
ccccgttcta tatcatcatt gagttcatga cctacg                              36
```